(12) United States Patent
Marrinucci

(10) Patent No.: US 10,545,151 B2
(45) Date of Patent: Jan. 28, 2020

(54) METHODS FOR ANALYZING RARE CIRCULATING CELLS

(71) Applicant: Epic Sciences, Inc., San Diego, CA (US)

(72) Inventor: Dena Marrinucci, San Diego, CA (US)

(73) Assignee: Epic Sciences, Inc., San Diego, CA (US)

( * ) Notice: Subject to any disclaimer, the term of this patent is extended or adjusted under 35 U.S.C. 154(b) by 0 days.

(21) Appl. No.: 15/120,502

(22) PCT Filed: Feb. 19, 2015

(86) PCT No.: PCT/US2015/016499
§ 371 (c)(1),
(2) Date: Aug. 19, 2016

(87) PCT Pub. No.: WO2015/127008
PCT Pub. Date: Aug. 27, 2015

(65) Prior Publication Data
US 2017/0010268 A1   Jan. 12, 2017

Related U.S. Application Data

(60) Provisional application No. 61/943,192, filed on Feb. 21, 2014.

(51) Int. Cl.
| C12Q 1/68 | (2018.01) |
| G01N 33/53 | (2006.01) |
| G01N 33/574 | (2006.01) |
| C12Q 1/6841 | (2018.01) |

(52) U.S. Cl.
CPC ..... *G01N 33/57423* (2013.01); *C12Q 1/6841* (2013.01); *G01N 2333/70589* (2013.01)

(58) Field of Classification Search
None
See application file for complete search history.

(56) References Cited

U.S. PATENT DOCUMENTS

| 6,197,523 B1 * | 3/2001 | Rimm ............... G01N 15/042 356/36 |
| 6,670,197 B2 | 12/2003 | Rimm et al. |
| 6,960,449 B2 | 11/2005 | Wang et al. |
| 7,277,569 B2 | 10/2007 | Bruce et al. |
| 7,280,261 B2 | 10/2007 | Curry et al. |
| 7,282,180 B2 | 10/2007 | Tibbe et al. |
| 7,305,112 B2 | 12/2007 | Curry et al. |
| 7,546,210 B2 | 6/2009 | Callahan et al. |
| 7,724,937 B2 | 5/2010 | So et al. |
| 7,943,397 B2 | 5/2011 | Tibbe et al. |
| 8,088,715 B2 | 1/2012 | Bodmer et al. |
| 2001/0018058 A1 | 8/2001 | Reed et al. |
| 2002/0098535 A1 | 7/2002 | Wang et al. |
| 2002/0160443 A1 | 10/2002 | Tsipouras et al. |
| 2002/0187485 A1 | 12/2002 | Jakobsen et al. |
| 2003/0108529 A1 | 6/2003 | Nackman et al. |
| 2003/0109059 A1 | 6/2003 | Adrien et al. |
| 2003/0109420 A1 | 6/2003 | Valkirs et al. |
| 2003/0129676 A1 | 7/2003 | Terstappen et al. |
| 2004/0029213 A1 | 2/2004 | Callahan et al. |
| 2005/0003464 A1 | 1/2005 | Tibbe et al. |
| 2005/0181463 A1 * | 8/2005 | Rao ............... G01N 33/54326 435/7.23 |
| 2006/0024756 A1 | 2/2006 | Tibbe et al. |
| 2007/0212698 A1 | 9/2007 | Bendele et al. |
| 2007/0212736 A1 | 9/2007 | Chen-Kiang et al. |
| 2008/0009019 A1 | 1/2008 | Haizlip et al. |
| 2008/0076727 A1 | 3/2008 | Hoon et al. |
| 2008/0090239 A1 | 4/2008 | Shoemaker et al. |
| 2008/0113358 A1 | 5/2008 | Kapur et al. |
| 2009/0029378 A1 * | 1/2009 | Connelly ........... G01N 21/6428 435/6.14 |
| 2009/0072171 A1 | 3/2009 | So et al. |
| 2009/0081688 A1 | 3/2009 | Luo et al. |
| 2009/0105963 A1 | 4/2009 | Laursen et al. |
| 2009/0317836 A1 * | 12/2009 | Kuhn ............... G01N 33/574 435/7.23 |
| 2010/0028915 A1 | 2/2010 | Gualberto et al. |
| 2010/0048709 A1 | 2/2010 | Wafa et al. |
| 2010/0184093 A1 | 7/2010 | Donovan et al. |
| 2010/0184629 A1 | 7/2010 | Giffin et al. |
| 2010/0297634 A1 | 11/2010 | Chen |
| 2010/0300216 A1 | 12/2010 | Angros |
| 2011/0189670 A1 | 8/2011 | Katz et al. |
| 2011/0238325 A1 | 9/2011 | Lett et al. |

(Continued)

FOREIGN PATENT DOCUMENTS

| CN | 1596265 A | 3/2005 |
| CN | 101099104 A | 1/2008 |

(Continued)

OTHER PUBLICATIONS

Jung et al, Bull. Korean Chem. Soc. 26 (3) 413 (2005).*
Hou et al, Scientific Reports 3: 1259 (Feb. 12, 2013).*
Stepanenko et al, PLOS one 7 (11), e48809 (Nov. 7, 2012).*
Damani et al., "Characterization of circulating endothelial cells in acute myocardial infarction," *Sci. Transl. Med.*, 4(126):126ra33 (2012).
Marrinucci et al., "Fluid biopsy in patients with metastatic prostate, pancreatic and breast cancers," *Phys. Biol.*, 9(1):016003 (2012).
Nieva et al., "High definition imaging of circulating tumor cells and associated cellular events in non-small cell lung cancer patients; a longitudinal analysis," *Phys. Biol.*, 9(1):016004 (2012).
Ren et al., "Detection of apoptotic circulating tumor cells in advanced pancreatic cancer following 5-fluorouracil chemotherapy," *Cancer Biol. Ther.*, 12(8):700-706 (2011).

(Continued)

*Primary Examiner* — James Martinell
(74) *Attorney, Agent, or Firm* — Jones Day

(57) ABSTRACT

The disclosure provides methods for analyzing rare circulating cells (RCCs) at cellular and molecular level following their detection in non-enriched blood samples, methods of this disclosure serve as diagnostic methods for several disease conditions, including cardiovascular diseases and cancer.

18 Claims, 8 Drawing Sheets

(56) References Cited

U.S. PATENT DOCUMENTS

| | | |
|---|---|---|
| 2011/0300551 A1 | 12/2011 | Rao et al. |
| 2012/0208706 A1 | 8/2012 | Downing et al. |
| 2012/0276555 A1 | 11/2012 | Kuhn et al. |
| 2013/0078667 A1 | 3/2013 | Goodman et al. |
| 2013/0130241 A1 | 5/2013 | Dehm |
| 2013/0157347 A1 | 6/2013 | Topol et al. |
| 2013/0171642 A1 | 7/2013 | Pestano et al. |
| 2013/0252259 A1 | 9/2013 | Kuhn et al. |
| 2014/0024024 A1* | 1/2014 | Sood ............... C12Q 1/6841 435/6.11 |
| 2014/0031250 A1 | 1/2014 | Ting et al. |
| 2014/0308669 A1 | 10/2014 | Yang et al. |
| 2014/0329917 A1 | 11/2014 | Marienfeld et al. |
| 2015/0147339 A1 | 5/2015 | Olson et al. |
| 2015/0185204 A1 | 7/2015 | Kuhn et al. |
| 2015/0212089 A1 | 7/2015 | Dittamore |
| 2015/0233927 A1 | 8/2015 | Giannakakou et al. |
| 2016/0033508 A1 | 2/2016 | Dittamore |
| 2016/0040245 A1 | 2/2016 | Dittamore |
| 2016/0266127 A1 | 9/2016 | Kuhn et al. |
| 2016/0341732 A1 | 11/2016 | Dittamore |
| 2017/0192003 A1 | 7/2017 | Kuhn et al. |
| 2017/0242016 A1 | 8/2017 | Dittamore |
| 2017/0285035 A1 | 10/2017 | Dittamore |
| 2018/0052167 A1 | 2/2018 | Dittamore |
| 2018/0100857 A1 | 4/2018 | Kuhn et al. |
| 2018/0155794 A1 | 6/2018 | Dittamore et al. |
| 2018/0321247 A1 | 11/2018 | Dittamore et al. |
| 2019/0025312 A1 | 1/2019 | Dittamore et al. |

FOREIGN PATENT DOCUMENTS

| | | |
|---|---|---|
| CN | 101511481 A | 8/2009 |
| CN | 101226118 B | 6/2010 |
| DE | 3830721 A1 | 3/1990 |
| EP | 0919812 A2 | 6/1999 |
| WO | WO 1999/41613 A1 | 8/1999 |
| WO | WO 2006/041453 A1 | 4/2006 |
| WO | WO 2007/008446 A2 | 1/2007 |
| WO | WO 2007/089911 A2 | 8/2007 |
| WO | WO 2008/030381 A2 | 3/2008 |
| WO | WO 2008/133666 A2 | 11/2008 |
| WO | WO 2009/051734 A1 | 4/2009 |
| WO | WO-2009120767 A1 * | 10/2009 |
| WO | WO 2011/050103 A1 | 4/2011 |
| WO | WO 2011/093927 A1 | 8/2011 |
| WO | WO 2012/103025 A2 | 8/2012 |
| WO | WO 2013/049926 A1 | 4/2013 |
| WO | WO 2013/086428 A1 | 6/2013 |
| WO | WO-2013111054 A * | 8/2013 |
| WO | WO 2013/181532 A1 | 12/2013 |
| WO | WO 2014/008155 A1 | 1/2014 |
| WO | WO 2014/066864 A2 | 5/2014 |
| WO | WO 2014/120265 A1 | 8/2014 |
| WO | WO 2014/151006 A2 | 9/2014 |
| WO | WO 2014/165785 A2 | 10/2014 |
| WO | WO 2015/048740 A1 | 4/2015 |
| WO | WO 2015/112955 A1 | 7/2015 |
| WO | WO 2015/112999 A1 | 7/2015 |
| WO | WO 2015/116828 A1 | 8/2015 |

OTHER PUBLICATIONS

Lin et al., "A negative selection system PowerMag for effective leukocyte depletion and enhanced detection of EpCAM positive and negative circulating tumor cells," Clinica Chem Acta, 419:77-84(2013).

Pestana et al., Improved diffuse fluorescence flow cytometer prototype for high sensitivity detection of rare circulating cells in vivo, J Biomed. Optics, 18(7):077002 (2013).

Aberle et al., "Reduced lung-cancer mortality with low-dose computed tomographic screening," N. Engl. J. Med., 365(5):395-409 (2011).

Abkevich et al., "Patterns of genomic loss of heterozygosity predict homologous recombination repair defects in epithelial ovarian cancer," Br. J. Cancer, 107(10):1776-1782 (2012).

Aggarwal et al., "Neuroendocrine prostate cancer: subtypes, biology, and clinical outcomes," J. Natl. Compr. Canc. Netw., 12(5):719-726 (2014).

Alix-Panabières et al., "Circulating tumor cells and circulating tumor DNA," Annu. Rev. Med., 63:199-215 (2012).

Alix-Panabières et al., "Circulating tumor cells: liquid biopsy of cancer," Clin. Chem., 59(1):110-118 (2013).

Allard et al., "Tumor cells circulate in the peripheral blood of all major carcinomas but not in healthy subjects or patients with nonmalignant diseases," Clin. Cancer Res., 10(20):6897-6904 (2004).

Amato et al., "Epithelial cell adhesion molecule-positive circulating tumor cells as predictive biomarker in patients with prostate cancer," Urology, 81(6):1303-1307 (2013).

Angerer et al., "Demonstration of tissue-specific gene expression by in situ hybridization," Methods Enzymol., 152:649-661 (1987).

Anonymous, "Circulating tumor cell," Wikipepia, Jan. 13, 2015, retrieved from the internet: URL:https://en.wikipedia.org/w/index.php?title=Circulating_tumor_cell&oldid=642235295 [retrieved on May 3, 2018], 14 pages.

Antonarakis et al., "Androgen Receptor Splice Variant 7 and Efficacy of Taxane Chemotherapy in Patients With Metastatic Castration-Resistant Prostate Cancer," JAMA Oncol., 1(5):582-591 (2015).

Antonarakis et al., "AR splice variant (AR-V7) and response to taxanes in men with metastatic castration-resistant prostate cancer (mCRPC)," J. Clin. Oncol., 33(7):138 (2015).

Antonarakis et al., "AR-V7 and resistance to enzalutamide and abiraterone in prostate cancer," N. Engl. J. Med., 371(11):1028-1038 (2014).

Aparico et al., "Platinum-based chemotherapy for variant castrate-resistant prostate cancer," Clin. Cancer Res., 19(13):3621-3630 (2013).

Ariosa Diagnostics Center, Inc. v. Sequenom, Inc., Opinion of the United States Court of Appeals for the Federal Circuit, pp. 1-21 (2015).

Armstrong et al., "Circulating tumor cells from patients with advanced prostate and breast cancer display both epithelial and mesenchymal markers," Mol. Cancer Res., 9(8):997-1007 (2011).

Armstrong et al., "Biomarkers in the management and treatment of men with metastatic castration-resistant prostate cancer," Eur. Urol., 64(3):549-559 (2012).

Arora et al., "Glucocorticoid receptor confers resistance to antiandrogens by bypassing androgen receptor blockade," Cell, 155(6):1309-1322 (2013).

Arya et al., "Enrichment, detection and clinical significance of circulating tumor cells," Lab. Chip., 13(11):1995-2027 (2013).

Asworth, "A case of cancer in which cells similar to those in the tumours were seen in the blood after death," Australian Med. J., 14:146-147 (1869).

Attard et al, "Utilizing circulating tumor cells: challenges and pitfalls," Curr. Opin. Gen. Dev., 21:50-58 (2011).

Attard et al., "Selective inhibition of CYP17 with abiraterone acetate is highly active in the treatment of castration-resistant prostate cancer," J. Clin. Oncol.,27(23):3742-3748 (2009).

Attard et al., "Characterization of ERG, AR and PTEN gene status in circulating tumor cells from patients with castration-resistant prostate cancer," Cancer Res., 69(7):2912-2918 (2009).

Autio et al., "Heterogeneity of prostate-specific membrane antigen expression in traditional and apoptotic circulating tumor cells in metastatic castration-resistant prostate cancer," American Society of Clinical Oncology Genitourinary (ASCO GU) conference, Jan. 30, 2014, San Francisco, CA, J. Clin. Oncol., 32(4):Abstract 198 (2014).

Balic et al., "Circulating tumor cells: from bench to bedside," Annu. Rev. Med., 63:31-44 (2013).

Balic et al., "Progress in circulating tumor cell capture and analysis: implications for cancer management," Expert Rev. Mol. Diagn., 12(3):303-312 (2012).

Balmana et al., "Phase I trial of olaparib in combination with cisplatin for the treatment of patients with advanced breast, ovarian and other solid tumors," Ann. Oncol., 25(8):1656-1663 (2014).

(56) References Cited

OTHER PUBLICATIONS

Bambury et al., "Characteristics of de novo reistance to androgen targeting therapeutics (AR TX) through circulating tumor cells (CTCS) analysis in metastatic castration resistant prostate cancer (MCRPC) patients," *Annals. Oncol.*, 25(Suppl. 4):iv58-iv84, Abstract 237P (2014).
Becker et al., "New frontiers in circulating tumor cell analysis: a reference guide for biomolecular profiling toward translational clinical use," *Int. J Cancer*, 134(11):2523-2533 (2014).
Beltran et al., "The initial detection and partial characterization of circulating tumor cells in neuroendocrine prostate cancer," *Clin. Cancer Res.*, 22(6):1510-1519 (2016).
Beltran et al., "Aggressive variants of castration-resistant prostate cancer," *Clin. Cancer Res.*, 20(11):2846-2850 (2014).
Beltran et al., "Challenges in recognizing treatment-related neuroendocrine prostate cancer," *J. Clin. Oncl.*, 30(36):e386-e389 (2012).
Beltran et al., "Molecular characterization of circulating tumor cells of patients with neuroendocrine prostate cancer," American Society of Clinical Oncology Genitourinary (ASCO GU) conference, Jan. 30, 2014, San Francisco, CA, J. Clin. Oncol., 32(4):Abstract 177 (2014).
Beltran et al., "Molecular characterization of neuroendocrine prostate cancer and identification of new drug targets," *Cancer Discov.*, 1(6):487-495 (2011).
Beltran et al., "New strategies in prostate cancer: translating genomics into the clinic," *Clin. Cancer Res.*, 19(3):517-523 (2013).
Borgen et al., "Use of automated microscopy for the deteection of disseminated tumor cells in bone marrow samples," *Cytometry*, 46:215-221 (2001).
Bovee et al., "Loss of heterozygosity and DNA ploidy point to a diverging genetic mechanism in the origin of peripheral and central chondrosarcoma," *Genes, Chromosomes & Cancer*, 26:237-246 (1999).
Box et al., "An analysis of transformations," *J. Royal Statist. Soc., Series B*, 26(2):211-243 (1964).
Brandt et al., "Isolation of prostate-derived single cells and cell clusters from human peripheral blood," *Cancer Res.*, 56(20):4556-4561 (1996).
Breiman, "Random Forests," *Machine Learning*, 45:5-32 (2001).
Brenner et al., "Gene expression analysis by massively parallel signature sequencing (MPSS) on microbead arrays," *Nat. Biotechnol.*, 18(6):630-634 (2000).
Brenner et al., "ETS Fusion Genes in Prostate Cancer," *Prostate Cancer: Biochemistry, Molecular Biology and Genetics*, Tindall ed., Springer, New York, 16:139-183 (2013).
Chan et al., "Dramatically elevated circulating tumor cell number in a patient with small cell neuroendocrine carcinoma of the prostate," *Arch. Pathol. Lab. Med.*, 134(1):120-123 (2010).
Chang et al., "High-risk prostate cancer-classification and therapy," *Nat. Rev. Clin. Oncol.*, 11(6):308-323 (2014).
Chang, "Treatment options for hormone-refractory prostate cancer," *Rev. Urol.*, 9(Suppl 2):S13-S18 (2007).
Chen et al., "Clinical significance of programmed death-1 ligand-1 expression in patients with non-small cell lung cancer: a 5-year-follow-up study," *Tumori*, 98(6):751-755 (2012) Abstract only.
Chinen et al., "Cytokeratin-based CTC counting unrelated to clinical follow up," *J. Thorac. Dis.*, 5(5):593-599 (2013).
Cho et al., "Characterization of circulating tumor cell aggregates identified in patients with epithelial tumors," *Phys. Biol.*, 9:016001 (2012).
Cloonan et al., "Stem cell transcriptome profiling via massive-scale mRNA sequencing," *Nat. Methods*,5(7):613-619 (2008).
Cohen et al., "Prognostic significance of circulating tumor cells in patients with metastatic colorectal cancer," *Ann. Oncol.*, 20(7):1223-1229 (2009).
Cohen et al., "Relationship of circulating tumor cells to tumor response, progression-free survival, and overall survival in patients with metastatic colorectal cancer," *J. Clin. Oncol.*, 26(19):3213-3221 (2008).
Cookson et al., "Castration-resistant prostate cancer: AUA Guideline," *J. Urol.*, 190(2):429-438 (2013).
Crespo et al., "Androgen receptor expression in circulating tumour cells from castration-resistant prostate cancer patients treated with novel endocrine agents," *Br. J. Cancer*, 112:1166-1174 (2015).
Cristofanilli et al., "Circulating tumor cells, disease progression, and survival in metastic breast cancer," *N. Engl. J. Med.*, 351(8):781-791 (2004).
Cristofanilli et al., "Circulating tumor cells: a novel prognostic factor for newly diagnosed metastatic breast cancer," *J. Clin. Oncol.*, 23(7): 1420-1430 (2005).
Cristofanilli, "The biological information obtainable from circulating tumor cells," *Breast*, 3:S38-S40.
Curry et al., "High-speed detection of occult tumor cells in peripheral blood," Proceedings at the 26th Annual International Conference of *IEEE EMBS*, San Francisco, CA, Sep. 1-5, 1267-1270 (2004).
Danila et al., "TMPRSS2-ERG status in circulating tumor cells as a predictive biomarker of sensitivity in castration-resistant prostate cancer patients treated with abiraterone acetate," Eur. Urol., 60(5):897-904 (2011).
Danila et al., "Circulating tumor cell number and prognosis in progressive castration-resistant prostate cancer," *Clin. Cancer Res.*, 13(23):7053-7058 (2007).
Danila et al., "Circulating tumors cells as biomarkers: progress toward biomarker qualification," *Cancer J.*, 17(6):438-450 (2011).
Darshan et al., "Taxane-induced blockade to nuclear accumulation of the androgen receptor predicts clinical responses in metastatic prostate cancer," *Cancer Res.*, 71(18):6019-6029 (2011).
De Bono et al., "Circutlating tumor cells predict survival benefit from treatmetn in metastatic castration-resistant prostate cancer," *Clin. Cancer Res.*, 14(19):6302-6309 (2008).
De Giorgi et al., "Application of a filtrationo- and isolation-by-size technique for the detection of circulating tumor cells in cutaneous melanoma," *J. Invest. Dermatol.*, 130:2440-2447 (2010).
Del Conte et al., "Phase I study of olaparib in combination with liposomal doxorubicin in patients with advanced solid tumours," *Br. J. Cancer*, 111(4):651-659 (2014).
Diamond et al., "Isolation and characterization of circulating tumor cells in prostate cancer," *Front Oncol.*, 2:131 (2012).
Dittamore et al., "Molecuar characterization of circulating tumor cells (CTCs) and CTC subpopulations in progressive metastatic castration-restitant prostate cancer (mCRPC)," American Society of Clinical Oncology Genitourinary (ASCO GU) conference, Jan. 30, 2014, San Francisco, CA, J. Clin. Oncol., 32(4):Abstract 132 (2014).
Etzioni et al., "The case for early detection," *Nature Rev.*, 3:1-10 (2003).
Evans et al., "Noninvasive measurement of androgen receptor signaling with a positron-emitting radiopharmaceutical that targets prostate-specific membrane antigen," *Proc. Natl. Acad. Sci. USA*, 108(23):9578-9582 (2011).
Fehm et al., "Methods for isolating circulating epithelial cells and criteria for their classification as carcinoma cells," *Cytotherapy*, 7(2):171-185 (2005).
Ferraldeschi et al., "CK-and small nuclear size circulating tumor cell phenotypes in metastatic castration-resistant prostate cancer," American Society of Clinical Oncology Genitourinary (ASCO GU) conference, Jan. 30, 2014, San Francisco, CA, J. Clin. Oncol., 32(4):Abstract 209 (2014).
Friedlander et al., "Detection and genomic interrogation of circulating tumor cells (CTCs) and circulating tumor stem cells (CTSCs) from men with metastatic castration-resistant prostate cancer (mCRPC)," *Eur. J. Cancer*, 48(Supp 6):152, Abstract 490 (2012).
Gazzaniga et al., "Circulating tumor cells: highlight on practical implications," *Mol. Diagn. Ther.*, 16(1):7-11 (2012).
Gibbs et al., "Abstract 4816: Development of an integrated analysis platform of circulating melanoma cells for PD-L1 expression as a predictive biomarker," *Cancer Res.*, 74(19 Suppl):Abstract 4816 (2014).
Giordano et al., "Epithelial-mesenchymal transition and stem cell markers in patients with HER2-positive metastatic breast cancer," *Mol. Cancer Ther.*, 11(11):2526-2534 (2012).

(56) References Cited

OTHER PUBLICATIONS

Giuliano et al., "Circulating tumor cells as early predictors of metastatic spread in breast cancer patients with limited metastatic dissemination," *Breast Cancer Res.*, 16(5):440 (2014).
Gorges et al., "Circulating tumor cells as therapy-related biomarkers in cancer patients," *Cancer Immunol. Immunother.*,62(5):931-939 (2013).
Gorges et al., "Circulating tumour cells escape from EpCAM-based detection due to epithelial-to-mesenchymal transition," *BMC Cancer*, 12:178 (2012).
Grasso et al., "The mutational landscape of lethal castration-resistant prostate cancer," *Nature*, 287(7406):239-243 (2012).
Gross et al., "Abstract 3630: Non-enrichment based method for analysis of androgen receptor expression in circulating tumor cells (CTCs) in patients with metastatic castrate resistant prostate cancer," Proceedings: AACR 103rd Annual Meeting, Chicago, IL Mar. 31-Apr. 4, 2012, Retrieved from the Internet: URL:http://cancerres.aacrjournals.org/content/72/8_Supplement/3630 [retrieved on Jun. 13, 2017], 3 pages.
Guo et al., "A new trick of an old molecule: androgen receptor splice variants taking the stage?!," *Int. J. Bio. Sci.*, 7(6):815-822 (2011).
Guo et al., "A novel androgen receptor splice variant is up-regulated during prostate cancer progression and promotes androgen depletion-resistant growth," *Cancer Res.*, 69(6):2305-2313 (2009).
Hager et al., "The use of a panel of monoclonal antibodies to enrich circulating breast cancer cells facilitates their detection," *Gynecol. Oncol.*, 98(2):211-216 (2005).
Hanash et al., "Mining the plasma proteome for cancer biomarkers," *Nature*, 452(7187):571-579 (2008).
Hao et al., "In vitro and in vivo prostate cancer metastasis and chemoresistance can be modulated by expression of either CD44 and CD147," *PLoS One*, 7(8):e40716 (2012).
Harada et al., "Androgen deprivation causes truncation of the C-terminal region of androgen receptor in human prostate cancer LNCaP cells," *Cancer Sci.*, 103:1022-1027 (2012).
Hofman et al., "Preoperative circulating tumor cell detection using the isolation by size of epithelial tumor cell method for patients with lung cancer is a new prognostic biomarker," 17(4):827-835 (2011).
Hsieh et al., "High speed detection of circulating tumor cells," *Biosen. Bioelectron.*, 21(10):1893-1899 (2006).
Ignatiadis et al., "Prognostic value of the molecular detection of circulating tumor cells using a multimarker reverse transcription-PCR assay for cytokeratin 19, mammaglobin A, and HER2 in early breast cancer," *Clin. Cancer Res.*, 14(9):2593-2600 (2008).
Ihaka et al., "A langauge for data analysis and graphics," *J. Comput. Graph. Statist.*, 5(3):299-314 (2012).
Ioannidis, "Why most published research findings are false," *PLoS Med.*, 2(8):e124 (2005).
Isakoff et al., "TBCRC009: A Multicenter Phase II Clinical Trial of Platinum Monotherapy With Biomarker Assessment in Metastatic Triple-Negative Breast Cancer," *J. Clin. Oncol.*, 33(17):1902-1909 (2015).
Jiang et al., "A comparison of isolated circulating tumor cells and tissue biopsies using whole-genome sequencing in prostate cancer," Oncotarget, 6(42):44781-44793 (2015).
Jiang et al., "Detection of androgen receptor mutations in circulating tumor cells in castration-resistant prostate cancer," Clin. Chem., 56(9):1492-1495 (2010).
Jilaveanu et al., "PD-L1 expression in clear cell renal cell carcinoma: an analysis of nephrectomy and sites of metastases," J. Cancer, 5(3):166-172 (2014).
Jones et al., "Wright-Giemsa cytology of body fluids," *Laboratory Medicine*, 28(11):713-716 (1997).
Joosse et al., "Biologic challenges in the detection of circulating tumor cells," *Cancer Res.*, 73(1):8-11 (2013).
Kalluri et al., "The basics of epithelial-mesenchymal transition," *J. Clin. Invest.*, 119(6):1420-1428 (2009).
Kang et al., "A combined micromagnetic-microfluidic device for rapid capture and culture of rare circulating tumor cells," *Lab. Chip.*, 12:2175-2181 (2012).
Kodiha et al., "Computer-based fluorescence quantification: a novel approach to study nucleolar biology," BMC Cell Biol., 12:25, 1-18 (2011).
Kolatkar et al., "C-ME: a 3D community-based, real-time collaboration tool for scientific research and training," *PLoS One*, 3(2):e1621 (2008).
Kraan et al., "A new approach for rapid and reliable enumeration of circulating endothelial cells in patients," *J. Thromb. Haemost.*, 10(5):931-939 (2012).
Kraeft et al., "Detection and analysis of lung cancer cells from body fluids using a rare event imaging system," *Methods Mol. Med.*, 75:423-430 (2003).
Kraeft et al., "Detection and anlysis of cancer cells in blood and bone marrow using a rare event imaging system," *Clin. Cancer Res.*, 6:434-442 (2000).
Kraeft et al., "Reliable and sensitive identificaiton of occult tumor cells using the improved rare event imaging system," *Clin. Cancer Res.*, 10(9):3020-3028 (2004).
Krebs et al., "Analysis of circulating tumor cells in patients with non-small cell lung cancer using epithelial marker-dependent and -independenent approaches," *J. Thorac Oncol.*, 7:306-315 (2012).
Krebs et al., "Evaluation and prognostic significance of circulating tumor cells in patients with non-small-cell lung cancer," *J. Clin. Oncol.*, 29(12): 1556-1563 (2011).
Krebs et al., "Molecular analysis of circulating tumour cells-biology and biomarkers," *Nat. Rev. Clin. Oncol.*, 11(3):129-144 (2014).
Krivacic et al., "A rare-cell detector for cancer," *PNAS USA*, 101(29):10501-10504 (2004).
Kryzwinski et al., "Circos: an information aesthetic for comparative genomics," *Genome Res.*, 19(9):1639-1645 (2009).
Kuhn et al., "A fluid biopsy as investigating technology for the fluid phase of solid tumors," *Phys. Biol.*, 9(1): 010301 (2012).
Larson et al., "Apoptosis of circulating tumor cells in prostate cancer patients," *Cytometry*, 62A:46-53 (2004).
Leversha et al., Fluorescence in situ hybridization analysis of circulating tumor cells in metastatic prostate cancer, *Clin. Cancer Res.*, 15(6):2091-2097 (2009).
Li et al., "Detection and validation of circulating endothelial cells, a blood-based diagnostic marker of acute myocardial infarction," *PLoS One*, 8(3):e58478 (2013).
Libertini et al., "Evidence for calpain-mediated androgen receptor cleavage as a mechanism for androgen independence," *Cancer Res.*, 67(19):9001-9005 (2007).
Ligthart et al., "Unbiased and automated identification of a circulating tumour cell definition that associates with overall survival," *PLoS One*, 6(11):e27419 (2011).
Lin et al., "Disseminated and circulating tumor cells: Role in effective cancer management," Crit. Rev. Oncol. Hematol., 77(1):1-11 (2011).
Lin et al., "Portable filter-based microdevice for detection and characterization of circulating tumor cells," *Clin. Cancer Res.*, 16(20):5011-5018 (2010).
Liotta et al., "The significance of hematogenous tumor cell clumps in the metastatic process," *Cancer Res.*, 36(3):889-894 (1976).
Lu et al., "Parylene membrane slot filter for the capture, analysis and culture of viable circulating tumor cells," IEEE 23rd International Conference, Piscataway, NJ, Jan. 24, 2010, pp. 935-938.
Lucci et al., "Circulating tumour cells in non-metastatic breast cancer: a prospective study," *Lancet Oncol.*, 13(7):688-695 (2012).
Luttgen et al., "Developing a non-invasive, diagnostic test for stage I non-small cell lung cancer using circulating tumor cells," AACR, Cancer Res., 73(8 Suppl):3485 (2013).
Ma et al., "Potent antitumor activity of an auristatin-conjugated, fully human monoclonal antibody to prostate-specific membrane antigen," *Clin. Cancer Res.*, 12(8):2591-2596 (2006).
Maheswaran et al., "Detection of mutations in EGFR in circulating lung-cancer cells," *N. Eng. J. Med.*, 359(4):366-377 (2008).
Marioni et al., "RNA-seq: an assessment of technical reproducibility and comparison with gene expression arrays," *Genome Res.*, 18(9):1509-1517 (2008).

(56) References Cited

OTHER PUBLICATIONS

Marquard et al., "Pan-cancer analysis of genomic scar signatures associated with homologous recombination deficiency suggests novel indications for existing cancer drugs," *Biomark Res.*, 3:9 (2015).
Marrinucci et al., "Bronchioloalveolar lung CTCs retain cytomorphologic features of primary tumor type," *J. Clin. Oncol.*, 26(15S):19118 (2008). Abstract only.
Marrinucci et al., "Case study of the morphologic variation of circulating tumor cells," *Hum. Pathol.*, 38(3):514-519 (2007).
Marrinucci et al., "Circulating tumor cells from well-differentiated lung adenocarcinoma retain cytomorphologic features of primary tumor type," *Arch. Pathol. Lab. Med.*, 133(9):1468-1471 (2009).
Marrinucci et al., "Cytomorphology of circulating colorectal tumor cells:a small case series," *J. Oncol.*, 2010:861341 (2010).
Mateo et al., "DNA-repair defects and olaparib in metastatic prostate cancer," *N. Engl. J. Med.*, 373(18):1697-1708 (2015).
Mateo et al., "The promise of circulating tumor cell analysis in cancer management," *Genome Biol.*, 15(8):448 (2014).
McDaniel et al., "Phenotypic diversity of circulating tumour cells in patients with metastatic castration-resistant prostate cancer," *BJU Int.*, 120(5B):E30-E44 (2017).
Medvedev et al., "Computational methods for discovering structural variation with next-generation sequencing," Nature Methods Supplement, 6(11s):S13-S20 (2009).
Melnikova et al., "Molecular characterizatoin of circulating tumor cells using a highly sensitive method of enrichment based on the CellSearch CTC profile kit," 22nd EORTC-NCI-AACR Symposium on Molecular Targets and Cancer; poster session, Jan. 1, 2010 (1 page).
Meng et al., "Circulating tumor cells in patients with breast cancer dormancy," *Clin. Cancer Res.*, 10(24):8152-8162 (2004).
Mercer, "Use of multiple markers to enhance clinical utility," *Immunol. Ser.*, 53:39-54 (1990).
Mezynski et al., "Antitumour activity of docetaxel following treatment with the CYP17A1 inhibitor abiraterone: clinical evidence for cross-resistance?," *Ann. Oncol.*, 23(11):2943-2947 (2012).
Mikolajczyk et al., "Detection of EpCAM-negative and cytokeratin-negative circulating tumor cells in peripheral blood," *J. Oncol.*, 2011:252361, 10 pages (2011).
Miller et al., "Significance of circulating tumor cells detected by the CellSearch System in patients with metastatic breast colorectal and prostate cancer," *J. Oncol.*, 2010:617421 (2010).
Miyake et al., "Alpha-fetoprotein and human chorionic gonadotropin-producing lung cancer," *Cancer*, 59(2):227-232 (1987).
Miyamoto et al., "Androgen receptor signaling in circulating tumor cells as a marker of hormonally responsive prostate cancer," *Cancer Discov.*, 2(11):995-1003 (2012).
Miyamoto et al., "Androgen receptor signaling in circulating tumor cells as a marker of hormonally responsive prostate cancer: supplemental methods single molecule sequencing and AR transcriptional signature," Retrieved from the internet: URL:http://http://cancerdiscovery.aacrjournals.org/content/suppl/2012/Sep. 14, 2159-8290.CD-12-0222.DC1. [retrieved on Apr. 16, 2019] DOI: 10.1158/2159-8290.CD-12-0222 (2012).
Mohamed et al., "Isolation of tumor cells using size and deformation," *J. Chromatogr. A.*, 1216(47):8289-8295 (2009).
Mohler et al., "Prostate cancer, version 1.2014," *J. Natl. Compr. Canc. Netw.*, 11(12):1471-1479 (2013).
Mohler et al., "Prostate cancer, version 2.2014," *J. Natl. Compr. Canc. Netw.*, 12(5):686-718 (2014).
Molnar et al., "Circulating tumor cells clusters in the peripheral blood of colorectal cancer patients," *Clin. Cancer Res.*, 7(12):4080-4085 (2001).
Morin et al., "Application of massively parallel sequencing to microRNA profiling and discovery in human embryonic stem cells," *Genome Res.*, 18(4):610-621 (2008).
Morrison et al., "Labeling fluorescence in situ hybridization probes for genomic targets," in *Molecular Cytogenetics: Protocols and Applications*, Y.S. Fan Ed., Humana Press, Chapter 2, pp. 21-40.

Mortazavi et al., "Mapping and quantifying mammalian transcriptomes by RNA-Seq," *Nat. Methods*, 5(7):621-628 (2008).
Mosquera et al., "Concurrent AURKA and MYCN gene amplifications are harbingers of lethal treatment-related neuroendocrine prostate cancer," *Neoplasia*, 15(1):1-10 (2013).
Mostaghel et al., "Molecular pathways: targeting resistance in the androgen receptor for therapeutic benefit," *Clin. Cancer Res.*, 20(4):791-798 (2014).
Mumford et al., "Circulating melanoma cells in the diagnosis and monitoring of melanoma: an appraisal of clinical potential," *Mol. Diang. Ther.*, 18(2):175-183 (2014).
Nagle et al., "ERG overexpression and PTEN status predict capsular penetration in prostate carcinoma," *Prostate*, 73(11):1233-1240 (2013).
Nagrath et al., "Isolation of rare circulating tumour cells in cancer patients by microchip technology," *Nature*, 450(7173):1235-1239 (2007).
Nagy et al., "Mulitiplexed protein and gene profiling of circulating tumor cells (CTCs) in metastatic castration-resistant prostate cancer (mCRPC) using automated immunofluorescence and fluorescence in situ hybridization," *J. Clin. Oncol.*, 31(6):Suppl. 1, Abstract No. 158, (2013).
Nair et al., "An observational study of circulating tumor cells and $^{18}$F-FDG PET uptake in patients with treatment-naive non-small cell lung cancer," *PLoS One*, 8(7):e67733 (2013).
Nair et al., "Clinical outcome prediction by microRNAs in human cancer: a systematic review," *J. Natl. Cancer Inst.*, 104(7): 528-540 (2012).
Noonan et al., "Clinical activity of abiraterone acetate in patients with metastatic castration-resistant prostate cancer progressing after enzalutamide," *Ann. Oncol.*, 024 Spec(7):1802-1807 (2013).
Olmos et al., "Circulating tumour cell (CTC) counts as intermediate end points in castration-resistant prostate cancer (CRPC): a single-centre experience," *Ann. Oncol.*, 20(1):27-33 (2009).
Ozkumur et al., "Inertial focusing for tumor antigen-dependent and -independent sorting of rare circulating tumor cells," *Sci. Transl. Med.*, 5(179):179ra47 (2013).
Pantel et al., "Circulating epithelial cells in patients with benign colon diseases," *Clin. Chem.*, 58(5):936-940 (2012).
Pantel et al., "The potential of circulating tumor cells as a liquid biopsy to guide therapy in prostate cancer," *Cancer Discov.*, 2(11):974-975 (2012).
Park et al., "Highly efficient assay of circulating tumor cells by selective sedimentation with a density gradient medium and microfiltration from whole blood," *Anal. Chem.*, 84:7400-7407 (2012).
Park et al., "Morphological differences between circulating tumor cells from prostate cancer patients and cultured prostate cancer cells," *PLoS One*, 9(1):e85264 (2014).
Parkinson et al., "Considerations in the development of circulating tumor cell technology for clinical use," *J. Transl., Med.*, 10:138 (2012).
Paterlini-Brechot et al., "Circulating tumor cells (CTC) detection: clinical impact and future directions," *Cancer Lett.*, 253:180-204 (2007).
Pecot et al., "A novel platform for detection of CK+ and CK− CTCs," *Cancer Discov.*, 1(7):580-586 (2011).
Pezaro et al., "Activity of cabazitaxel in castration-resistant prostate cancer progressing after docetaxel and next-generation endocrine agents," *Eur. Urol.*, 66(3):459-465 (2014).
Phillips et al., "Physical biology in cancer. 2. The physical biology of circulating tumor cells," *Am. J. Physiol. Cell Physiol.*, 306(2):C80-C88 (2014).
Picard et al., "Cross-validation of regression models," *J. Am. Statist. Assoc.*, 79(387):575-583 (1984).
Pierga et al., "High independent prognostic and predictive value of circulating tumor cells compared with serum tumor markers in a large prospective trial in first-line chemotherapy for metastatic breast cancer patients," *Annals. Oncol.*, 23:618-624 (2012).
Polzer et al., "Molecular profiling of single circulating tumor cells with diagnostic intention," *EMBO Mol. Med.*, 6(11):1371-1386 (2014).

(56) References Cited

OTHER PUBLICATIONS

Popova et al., "Ploidy and large-scale genomic instability consistently identify basal-like breast carcinomas with BRCA1/2 inactivation," *Cancer Res.*, 72(21):5454-5462 (2012).
Punnoose et al., "Evaluation of circulating tumor cells and circulating tumor DNA in non-small cell lung cancer: association with clincal endpoints in a phase II clinical trial of pertuzumab and erlotinib," *Clin. Cancer Res.*, 18(8):1-11 (2012).
Punnoose et al., "PTEN loss in circulating tumour cells correlates with PTEN loss in fresh tumour tissue from castration-resistant prostate cancer patients," *Br. J. Cancer*, 113(8):1226-1233 (2015).
Qimaging, "Retiga EXi Fast 1394 User's Manual," Quantitative Imaging Corporation, (2003).
Racila et al., "Detection and characterization of carcinoma cells in the blood," *Proc. Natl. Acad. Sci. USA*, 95(8):4589-4594 (1998).
Rami-Porta et al., "The IASLC Lung Cancer Staging Project: proposals for the revision of the T descriptors in the forthcoming (seventh) edition of the TNM classification for lung cancer," *J. Thorac. Oncol.*, 2(7):593-602 (2007).
Rathkopf et al., "Androgen receptor antagonists in castration-resistant prostate cancer," *Cancer J.*, 19(1):43-49 (2013).
Reyal et al., "Circulating tumor cell detection and transcriptomic profiles in early breast cancer patients," *Ann. Oncol.*, 22(6):1458-1459 (2011).
Reyes et al., "Quantitative characterization of androgen receptor protein expression and cellular localization in circulating tumor cells from patients with metastatic castration-resistant prostate cancer," *J. Transl. Med.*, 12(1):313 (2014).
Rickman et al., "ERG cooperates with androgen receptor in regulating trefoil factor 3 in prostate cancer disease progression," Neoplasia, 12(12):1031-1040 (2010).
Riethdorf et al., "Detection of circtulating tumor cells in peripheral blood of patients with metastatic breast cancer: a validation study of the CellSearch System," *Clin. Cancer Res.*, 13(3):920-928 (2007).
Robinson et al., "Integrative clinical genomics of advanced prostate cancer," *Cell*, 161(5):1215-1228 (2015).
Romsdahl et al., "The time of metastasis and release of circulating tumor cells as determined in an experimental system," *Cancer*, 14:883-888 (1961).
Roudier et al., "Phenotypic heterogeneity of end-stage prostate carcinoma metastatic to bone," *Hum. Pathol.*, 34(7):646-653 (2003).
Santoni et al., "Neuroendocrine differentiation in prostate cancer: novel morphological insights and future therapeutic perspectives," *Biochim. Biophys. Acta.*, 1846(2):630-637 (2014).
Scheel et al., "Cancer stem cells and epithelial-mesenchymal transition: concepts and molecular links," *Semin. Cancer Biol.*, 22(5-6):396-403 (2012).
Scher et al., "Association of AR-V7 on Circulating Tumor Cells as a Treatment-Specific Biomarker With Outcomes and Survival in Castration-Resistant Prostate Cancer," *JAMA Oncol.*, 2(11):1441-1449 (2016).
Scher et al., "Baseline CTC subtype to predict outcomes on mCRPC patients (pts) receiving enzalutamide (E) compared to abiraterone (A)," *J. Clin. Oncol.*, 35(Suppl.15):5070 (2017).
Scher et al., "Characterization of circulating tumor cells (CTCS) of metastatic castration resistant prostte cancer (MCRPC) patients in first, second & third line systemic therapies," *Annals Oncol.*, 25(Suppl. 4):iv58-iv84, Abstract 238P (2014).
Scher et al., "Circulating tumour cells as prognostic markers in progressive, castration-resistant prostate cancer: a reanalysis of IMMC38 trial data," *Lancet Oncol.*, 10(3):233-239 (2009).
Schreuder, "Laser Image Cytometer for Analysis of Circulating Tumor Cells," Wöhrmann Print Sevice, Zutphen, The Netherlands, 166 pages (2008).
Schultz et al., "Validation of two models to estimate the probability of malignancy in patients with solitary pulmonary nodules," *Thorax*, 63(4):335-341 (2008).
Scotton et al., "Epithelial cancer cell migration: a role for chemokine receptors?," *Cancer Res.*, 61(13):4961-4965 (2001).

Self et al., "Advances in immunoassay technology," *Curr. Opin. Biotchnol.*, 7(1):60-65 (1996).
Shaffer et al., "Circulating tumor cell analysis in patients with progressive castration-resistant prostate cancer," *Clin. Cancer Res.*, 13(7):2023-2029 (2007).
Shah et al., "Androgen-independent prostate cancer is a heterogeneous group of diseases: lessons from a rapid autopsy program," *Cancer Res.*, 64(24):9209-9216 (2004).
Shankar et al., "Consensus recommendations for the use of $^{18}$F-FDG PET as an indicator of therapeutic response in patients in National Cancer Institute Trials," *J. Nucl. Med.*, 47(6):1059-1066 (2006).
Sidaway, "Non-traditional CTCs indicate prognosis," *Nature Rev.*, 13(7):592 (2016).
Siegel et al., "Cancer statistics, 2014," *CA Cancer J. Clin.*, 64(1):9-29 (2014).
Somlo et al., "Multiple biomarker expression on circulating tumor cells in comparison to tumor tissues from primary and metastatic sites in patients with locally advanced/inflammatory, and stage IV breast cancer, using a novel detection techonlogy," *Breast Cancer Res. Treat.*, 128(1):155-163 (2011).
Stanbrough et al., "Prostatic intraepithelial neoplasia in mice expressing an androgen receptor transgene in prostate epithelium," Proc. Natl. Acad. Sci USA, 98(19):10823-10828 (2001).
Starlinger et al., "Discrimination between circulating endothelial cells and blood cell populations with overlapping phenotype reveals distinct regulation and predictive potential in cancer therapy," *Neoplasia*, 13(10):980-990 (2011).
State of the Science Report, Highlights from the 19th Annual PCF Scientific Retreat, Oct. 2012, 21 pages.
Stemcell Technologies, "Frequencies of Cell Types in Human Peripheral Blood," retrieved on Jun. 8, 2012, via Wayback Machine, 1 page.
Stott et al., "Isolation of circulating tumor cells using a microvortex-generating herringbone-chip," Proc. Natl. Acad. Sci. USA, 107(43):18392-18397 (2010).
Stott et al., "Isolation and characterization of circulating tumor cells from patients with localized and metastic prostate cancer," *Sci. Transl. Med.*, 2(25):25ra23 (2010).
Strijbos et al., "Circulating endothelial cells in oncology: pitfalls and promises," *Br. J. Cancer*, 98:1731-1735 (2008).
Tagawa, "Neuroendocrine prostate cancer after hormonal therapy: knowing is half the battle," *J. Clin. Oncol.*, 32(30):3360-3364 (2014).
Takahashi, "An experimental study of metastasis," *J. Path. Bacter.*, 20(1): 1-13 (1915).
Tanaka et al., "Monoclonal antibody targeting of N-cadherin inhibits prostate cancer growth, metastasis and castration resistance," *Nat. Med.*, 16(12):1414-1420 (2010).
Tanaka et al., "Circulating tumor cell as a diagnostic marker in primary lung cancer," *Clin. Cancer Res.*, 15(22):6980-6986 (2009).
Tanaka et al., "Circulating tumor cells (CTCs) in lung cancer: current status and future perspectives," *Lung Cancer: Targets and Therapy*, 1:77-84 (2010).
Theodoropoulo et al., "Circulating tumor cells with a putative stem cell phenotype in peripheral blood of patients with breast cancer," *Cancer Letts.*, 288:99-106 (2010).
Tibshirani, "Regression shrinkage and selection via the lasso," *J. Royal Statist Soc.*, Series B, 58(1):267-288 (1996).
Tockman et al., "Considerations in bringing a cancer biomarker to clinical application," *Cancer Res.*, 52:2711s-2718s (1992).
Tufman et al., "Biological markers in lung cancer: a clinician's perspective," *Cancer Biomarkers*, 6(3-4):123-135 (2009).
Ulmer et al., "Immunomagnetic enrichment, genomic characterization, and prognostic impact of circulating melanoma cells," *Clin. Cancer Res.*, 15(2):531-537 (2004).
Vincent et al., "Carcinoembryonic antigen in 228 patients with carcinoma of the lung," *Cancer*, 36(6):2069-2076 (1975).
Vollebergh et al., "Genomic patterns resembling BRCA1- and BRCA2-mutated breast cancers predict benefit of intensified carboplatin-based chemotherapy," *Breast Cancer Res.*, 16(3):R47 (2014).

(56) References Cited

OTHER PUBLICATIONS

Vona et al., "Enrichment, immunomorphological, and genetic characterization of fetal cells circulating in maternal blood," Am. J. Pathol., 160(1):51-58 (2002).
Vona et al., "Isolation by size of epithelial tumor cells : a new method for the immunomorphological and molecular characterization of circulatingtumor cells," *Am. J. Pathol.*, 156(1):57-63 (2000).
Wang et al., "Identification and characterization of circulating prostate carcinoma cells," *Cancer,* 88(12):2787-2795 (2000).
Watanabe et al., "Multicolor detection of rare tumor cells in blood using a novel flow cytometry-based system," *Cytometry A.*, 85(3):206-213 (2014).
Waters, "Accuracy and precision in quantitative fluorescence microscopy," *J. Cell Biol.,* 185(7):1135-1148 (2009).
Watkins et al., "Genomica scars as biomarkers of homologous recombination deficiency and drug response in breast and ovarian cancers," *Breast Cancer Res.,* 16(3):211 (2014).
Wendel et al., "Fluid biopsy for circulating tumor cell identification in patients with early-and late-stage non-small cell lung cancer: a glimpse into lung cancer biology," *Phys. Biol.,* 9(1):016005 (2012).
Werner et al., "Analytical Validation and Capabilities of the Epic CTC Platform: Enrichment-Free Circulating Tumour Cell Detection and Characterization," *J. Circ. Biomark.,* 4:3 (2015).
Witzig et al., "Detection of circulating cytokeratin-positive cells in the blood of breast cancer patients using immunomagnetic enrichment and digital microscopy," *Clin. Cancer Res.,* 8(5):1085-1091 (2002).
Wong et al., "Evolution of androgen receptor targeted therapy for advanced prostate cancer," *Nat. Rev. Clin. Oncol.,* 11:365-376 (2014).
Woywodt et al., "Isolation and enumeration of circulating endothelial cells by immnomagnetic isolation: proposal of a definition and a consensus protocol," *J. Thromb. Heaemost.,* 4:671-677 (2006).
Yap et al., "Circulating tumor cells: a multifunctional biomarker," *Clin. Cancer Res.,* 20(10):2553-2568 (2014).
Yu et al., "Circulating tumor cells: approaches to isolation and the characterization," J. Cell Biol., 192(3):373-382 (2011).
Yu et al., "Circulating breast tumor cells exhibit dynamic changes in epithelial and mesenchymal composition," *Science,* 339(6119):580-584 (2013).
Zafarana et al., "Copy number alterations of c-MYC and PTEN are prognostic factors for relapse after prostate cancer radiotherapy," *Cancer,* 118(16):4053-4062 (2012).
Zhang et al., "Androgen receptor variants occur frequently in castration resitant prostate cancer metastases," PLoS ONE, 6(11):e27970 (2011).
Zhang et al., "The identification and characterization of breast cancer CTCs competent for brain metastasis," *Sci. Transl. Med.,* 5(180):180ra48 (2013).
Zhao et al., CN 101226118 b, machine translation to English, 2010, 22 pages.
Zhau et al., "Epithelial to mesenchymal transition (EMT) in human prostate cancer: lessons learned from ARCaP model," *Clin. Exp. Metastasis,* 25(6):601-610 (2008).
Zheng et al., "Level of circulating PD-L1 expression in patients with advanced gastric cancer and its clinical implications," Chin. J. Cancer Res., 26(1):104-111 (2014).
Zheng et al., "Membrane microfilter device for selective capture, electrolysis and genomic analysis of human circulating tumor cells," *J. Chromatogr.,* 1162(2):154-161 (2007).
Zhang et al., "A genomic instability score in discriminating nonequivalent outcomes of BRCA1/2 mutations and in predicting outcomes of ovarian cancer treated with platinum-based chemotherapy," PLoS One, 9(12):e113169 (2013).
Zlotta et al., "Prevalence of prostate cancer on autopsy: cross-sectyional study on unscreened Caucasian and Asian men," *J. Natl. Cancer Inst.,* 105(14):1050-1058 (2013).

\* cited by examiner

METHODS FOR ANALYZING RARE CIRCULATING CELLS

This application is a U.S. National Stage Application under 35 U.S.C. § 371 of International Patent Application No. PCT/US2015/016499, filed Feb. 19, 2015, which claims the benefit of priority of U.S. provisional application Ser. No. 61/943,192, filed Feb. 21, 2014, the entire contents of each of which are incorporated herein by reference.

The present disclosure relates generally to methods for the diagnosis of diseases such as cancer or cardiovascular diseases and, more specifically, to methods for the molecular and cellular analysis of rare circulating cells (RCCs), such as Circulating Tumor Cells (CTCs) or Circulating Endothelial Cells (CECs).

BACKGROUND

Certain types of rare cells circulating in the bloodstream (rare circulating cells, RCCs) have recently emerged as highly promising biomarker candidates in a growing number of disease conditions. For example, Circulating Tumor Cells (CTCs) are considered promising diagnostic and prognostic markers for the monitoring of cancer progression and anti-cancer treatment responses. Moreover, Circulating Endothelial Cells (CECs) are considered promising diagnostic and prognostic markers in cardiovascular disease conditions, such as acute myocardial infarction.

RCCs can be conveniently collected in blood samples ("liquid biopsy"), which enables repeated sampling throughout the course of a patient's disease progression or treatment regimen. Consequently, diagnostic methods based on RCC detection, quantification and analysis enable the real-time and personalized assessment of an individual patient's disease, which facilitates the design of personalized treatment plans.

However, the development of full biomarker utility of RCCs has been hindered by the lack of assay technologies that can accurately and robustly identify and enumerate RCCs and also allow for the downstream analysis of RCC cell biology (e.g., gene expression, metabolic activity, protein localization, RNA localization) and RCC molecular biology (e.g., genome, proteome, secretome, metabolome analysis). Especially the extremely low abundance of RCCs and the tremendous heterogeneity of RCC populations have posed substantial technical challenges for the development of reliable diagnostic assays.

Most existing RCC assay platforms lack the sensitivity and accuracy to allow for robust RCC identification and quantification. Moreover, the vast majority of RCC assay platforms do not allow for the detailed cellular or molecular analysis of RCCs once these cells have been identified and enumerated.

For example, many methods for RCC identification and quantification rely on flow cytometry (e.g., FACS) or immunocapture technologies (e.g., CellSearch®). While flow cytometry generally enables cell sorting, it cannot robustly enumerate very small populations of cells, such as CTCs or CECs (~1-10 CTCs/ml whole blood), in the presence of much more abundant cell populations, such as the white blood cell population (WBC; >1 million CTCs/ml whole blood). Additionally, FACS-based methods do not allow for the indepth analysis of cell morphologies.

One prominent example of RCC immunocapture platforms is the CellSearch® platform, which has obtained FDA-approval for the monitoring of metastatic cancer patients. The CellSearch® CTC immunocapture assay has recently been adapted for CEC detection (see, e.g., Damani, et al., 2012, Sci. Tansl. Med. 4, 126 ra33). However, CellSearch® and related immunocapture platforms require an initial immunomagnetic bead-based capture step that targets a single biomarker to enrich the very rare RCCs in a sample prior to an attempted identification and quantification. It is this initial, targeted enrichment step that render an unbiased multi-parametric analysis and classification of heterogeneous RCC populations impossible and that prevents any analysis from reaching much beyond the analysis of the single biomarker used for cell capture. Moreover, RCC-targeted immunocapture assays are often plagued by a lack of assay sensitivity and specificity.

Due to the limitations of many existing assay technologies, the RCC levels reported for human blood samples vary greatly across the literature, even though substantial assay optimization and standardization efforts were made. This variability in RCC assay results significantly impedes the further development of RCCs as clinically useful biomarkers. Another caveat of most existing RCC assay technologies is the limited amount of diagnostically relevant information that is commonly obtained. Typical RCC assays may deliver RCC counts and describe general morphological features of a cell (e.g., cell size, size distributions across a cell population), but current RCC assays typically do not provide a diagnostically meaningful profile of RCC cell biology (e.g., regarding the energy metabolism of cancer cells or the presence of apoptotic bodies) or RCC molecular biology (e.g., presence of genetic abnormalities, including gene fusions, aneuploidy, loss of chromosomal regions, specific oncogene mutations or oncogene expression levels). Thus, new approaches are needed to accurately identify, enumerate and analyze RCCs.

Recently, a high-definition (HD) immunofluorescence assay platform has been developed, which enables the reliable identification and enumeration of RCCs in the presence of much more abundant cell types. HD-RCC assays are generally based on the side-by-side comparison of rare cells (e.g., CTCs or CECs) and abundant cells (e.g., WBCs) in non-enriched samples (e.g., blood samples) with respect to certain immunofluorescent and morphological characteristics. Most notably, HD-CTC and HD-CEC assays have proven to enable the highly sensitive, highly accurate, and highly robust detection and quantification of CTCs and CECs.

While current HD-RCC assay protocols enable accurate cell identification and cell counting, robust protocols for the subsequent downstream analysis of RCC cell biology or RCC molecular biology are still largely lacking today. Nevertheless, it is widely expected that a deeper understanding of RCC biology will promote the development of meaningful disease diagnostics and efficacious treatments. For example, it is expected that a better understanding of CTC biology will promote the development of next-generation anti-cancer treatments that target CTCs and thereby help suppress tumor metastasis. Moreover, it is expected that the detection of certain molecular characteristics of CTCs will have immediate diagnostic value (e.g., detection of BRCA-1/2 mutations) and aid in the personalized tailoring of anti-cancer treatment regimens to each patient (e.g., treatment with PARP inhibitors).

Thus, there exists a need for methods enabling the cellular and molecular analysis of RCCs following RCC detection. The present disclosure addresses this need by providing methods for the analysis of RCCs in non-enriched patient samples. Related advantages are provided as well.

SUMMARY

The present disclosure provides methods for further characterizing CTCs following their identification in a non-enriched biological sample In one aspect, the disclosure provides a method for analyzing rare circulating cells (RCCs) in a non-enriched blood sample, including: (a) detecting RCCs in the non-enriched blood sample, including i) determining presence or absence of one or more immunofluorescent RCC detection markers in nucleated cells in the non-enriched blood sample, and ii) assessing the morphology of the nucleated cells, wherein RCCs are detected among the nucleated cells based on a combination of distinct immunofluorescent staining and morphological characteristics; (b) quenching the immunofluorescence of the one or more immunofluorescent RCC detection markers including contacting the RCCs with a quenching buffer, wherein the immunofluorescence is quenched by more than 50%, 60%, 70%, 80%, 90%, 95%, 99%, 99.9% or 99.99%; and (c) analyzing the detected RCCs, comprising determining presence or absence of one or more fluorescent RCC analysis markers.

In some embodiments, the fluorescent RCC analysis markers are fluorescence in situ hybridization (FISH) markers.

In some embodiments, more than 25%, 30%, 35%, 40%, 45%, 50%, 55%, 60%, 65%, 70%, 75%, 80%, 85%, 90%, 95% or 99% of RCCs detected in (a) are retained in (c).

In some embodiments, the fluorescent RCC analysis markers are positive control markers. In some embodiments, the positive control markers are present in more than 25%, 30%, 35%, 40%, 45%, 50%, 55%, 60%, 65%, 70%, 75%, 80%, 85%, 90%, 95% or 99% of RCCs analyzed in (c). In some embodiments, the positive control markers are chromosomal markers. In some embodiments, the positive control markers are centromer markers or telomere markers.

In some embodiments, the fluorescent RCC analysis markers are genetic mutations selected from the group consisting of gene translocation, gene amplification gene deletion, gene aneuploidy and chromosomal aneuploidy.

In some embodiments, analyzing the detected RCCs further comprises assessing the morphology of the detected RCCs.

In some embodiments, the RCCs are circulating tumor cells (CTC). In some embodiments, the RCCs are a circulating epithelial cell (CEC). In some embodiments, the RCCs are CTC mimics. In some embodiments, the RCCs are CTC candidates.

In some embodiments, the quenching buffer comprises a chaotropic agent. In some embodiments, the concentration of the chaotropic agent is at least 2M, 3M or 4M. In some embodiments, the quenching buffer comprises a chaotropic salt. In some embodiments, the quenching buffer comprises guanidine or a guanidinium salt. In some embodiments, the quenching buffer comprises guanidinium thiocyanate (guanidine thiocyanate) or guanidinium chloride (guanidine hydrochloride).

In some embodiments, the method is performed by fluorescent scanning microscopy.

In some embodiments, the microscopy provides a field of view comprising more than 2, 5, 10, 20, 30, 40 or 50 RCCs, wherein each RCC is surrounded by more than 10, 50, 100, 150 or 200 WBCs.

In some embodiments, determining presence or absence of the immunofluorescent RCC detection markers comprises comparing the distinct immunofluorescent staining of RCCs with the distinct immunofluorescent staining of WBCs.

In some embodiments, determining presence or absence of the fluorescent RCC analysis markers comprises comparing the distinct fluorescent staining of RCCs with the distinct fluorescent staining of WBCs.

In some embodiments, assessing the morphology of the nucleated cells comprises comparing the morphological characteristics of RCCs with the morphological characteristics of surrounding WBCs.

DETAILED DESCRIPTION

The present disclosure is based, in part, on the discovery that RCCs can be subjected to further analysis of their cellular or molecular characteristics after they were identified, classified (e.g., as CTCs, CTC mimics, CTC candidates or CECs) and quantified in a non-enriched biological sample. Specifically, the present disclosure is based, in part, on the discovery that RCCs, such as CTCs, CTC mimics, CTC candidates or CECs, can be subjected to further analysis after they were identified, classified and quantified in a non-enriched biological sample using an HD-RCC assay.

In certain embodiments, HD-RCC assays include, inter alia, detecting RCCs in non-enriched blood samples by determining presence or absence of certain immunofluorescent RCC detection markers. For example, the detection of CTCs can include determining the presence or absence of the immunofluorescent marker cytokeratin. In another example, the detection of CECs can include determining the presence or absence of the immunofluorescent detection marker Von Willebrand factor (vWF).

The present disclosure is further based, in part, on the discovery that in HD-RCC assays, the RCCs can be further analyzed by determining presence or absence of certain immunofluorescent RCC analysis markers. For example, in some embodiments, RCCs can be further analyzed by determining presence or absence of oncogene mutations or of elevated oncogene expression levels. In some embodiments, determining presence or absence of RCC analysis markers includes in situ fluorescence hybridization (FISH).

The present disclosure is further based, in part, on the discovery that, in some embodiments, determining the presence or absence of an immunofluorescent RCC analysis marker requires quenching the immunofluorescence of an immunofluorescent RCC detection marker.

Figure 2:
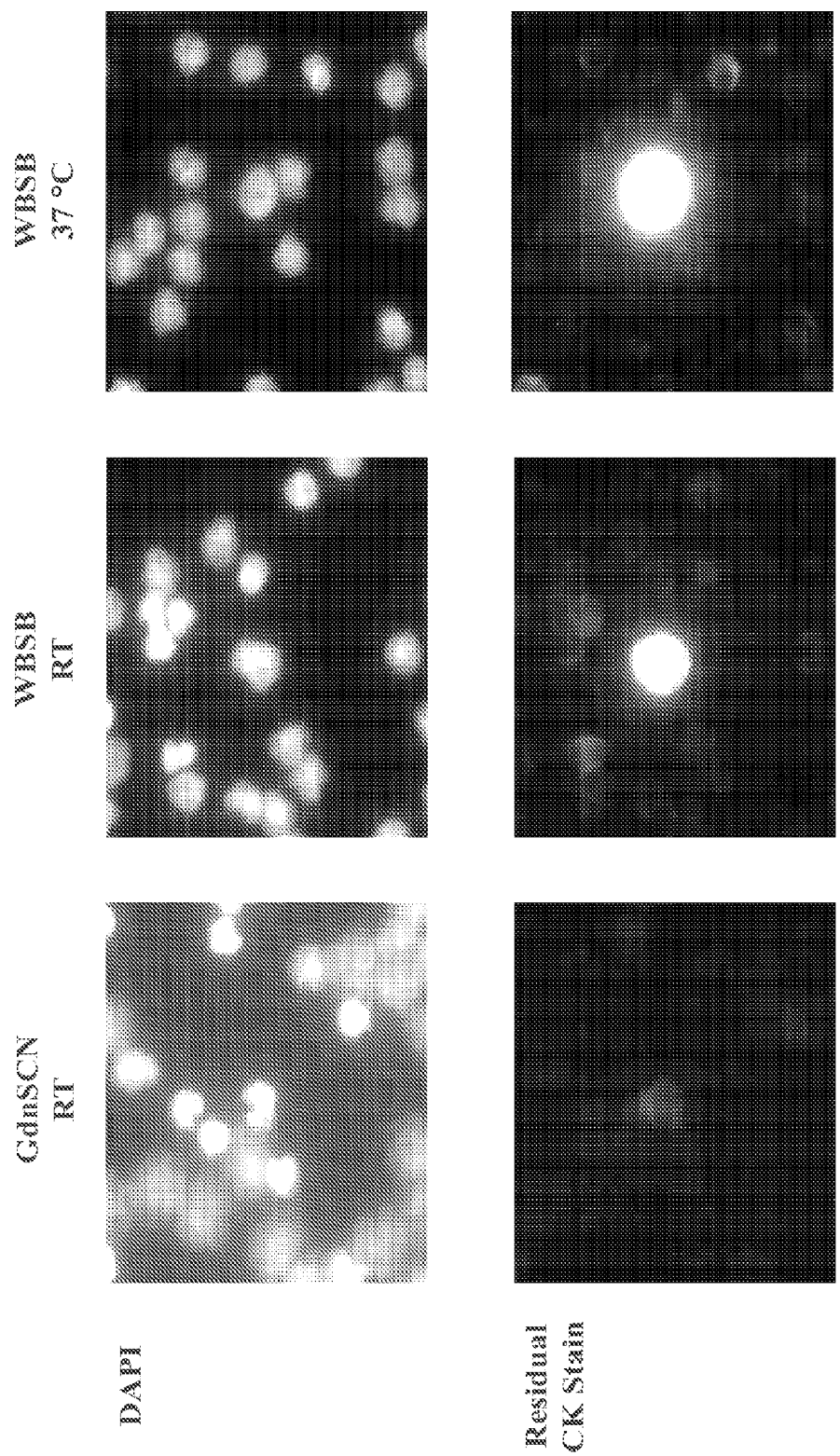
FIG. 2 shows images further illustrating the relative quenching effects of Guanidinium Thiocyanate Buffer (GdnSCN, 4M) and Western Blot Stripping Buffer (WBSB) on CTC immunofluorescence staining. Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (first column) at room temperature (RT) or after treatment with WBSB at room temperature (second column) or at 37° C. (third column).

The present disclosure is further based, in part, on the discovery that it is technically very challenging to effectively quench the immunofluorescence of an immunofluorescent RCC detection marker while, at the same time, retaining RCCs for subsequent analysis and while maintaining the RCCs in a condition that allows for the subsequent detection of immunofluorescent RCC detection markers. For example, it was found that many quenching buffers and many assay buffers (e.g., FISH buffers) that are commonly used by skilled artisans either did not sufficiently quench the immunofluorescence of RCC detection marker (see, e.g., FIG. 2; Western Blot Stripping Buffer, WBSB) or resulted in the loss of previously detected RCCs or rendered the remaining RCCs in a condition that did not allow for the subsequent detection of immunofluorescent RCC analysis markers or rendered the downstream analysis of RCCs otherwise impossible (see, e.g., FIG. 5, Glycine Buffer (pH 2)).

The present disclosure is further based, in part, on the surprising discovery that the immunofluorescence of an RCC detection marker can in fact be quenched while retaining a substantial number of RCCs for further analysis.

The present disclosure is further based, in part, on the surprising discovery that the presence of certain immunofluorescent RCC analysis markers can be detected in a substantial number of RCCs after the immunofluorescence of an immunofluorescent RCC detection marker has been quenched.

The present disclosure is further based, in part, on the surprising discovery that highly effective quenching buffers included buffers that a skilled artisan would not expect to yield high quality results when applied in a method of this disclosure, for example and without wishing to be bound by theory, because the buffers would be considered highly stressful or disruptive on cells and resulting in either cell loss or loss of RCC analysis marker signals (e.g., buffers containing chaotropic reagents).

The present disclosure is further based, in part, on the surprising discovery that the morphological characteristics of RCCs as well as other nucleated cells in the sample (e.g., white blood cells, WBCs) can be largely maintained after treatment of RCCs with effective quenching buffers that contain chaotropic agents, such as guanidinium thiocyanate and the like.

A fundamental aspect of the present disclosure is the robustness of the disclosed methods. The rare event detection (RED) disclosed herein with regard to RCCs is based on a direct analysis of a non-enriched cell population that encompasses the identification of rare events in the context of the surrounding non-rare events. Identification of the rare events according to the disclosed methods inherently identifies the surrounding events as non-rare events. Taking into account the surrounding non-rare events and determining the averages for non-rare events, for example, average cell size of non-rare events, allows for calibration of the detection method by removing noise. The result is a robustness of the disclosed methods that cannot be achieved with methods that are not based on direct analysis but that instead compare enriched populations with inherently distorted contextual comparisons of rare events.

The disclosure provides methods for further analyzing RCCs (e.g., CTCs, CTC mimics, CTC candidates or CECs) after they were identified in non-enriched blood samples. One major advantage of the present disclosure is the combination of a highly accurate and sensitive method for identifying, classifying and quantifying RCCs with downstream methods for analyzing RCCs with respect to their cell biology and molecular biology traits. In certain aspects the downstream analysis RCCs includes the analysis of disease and biomarkers, e.g., the detection of oncogene mutations (e.g., BRCA-1/2 mutations) in CTCs or the detection of aberrant oncogene expression levels (e.g., HER2 expression levels) in CTCs. It is widely expected that by combining an accurate RCC quantification with the downstream detection of disease markers or biomarkers the diagnostic and prognostic value of RCCs will be potentiated.

As a result, the present disclosure is of particular benefit, for example, to human patients. Specifically, cancer patients will benefit from the improved diagnosis of their disease. For example, the methods of this disclosure will improve the diagnosis of neoplastic progression or recurrence and allow for the real-time analysis of a tumor's development at the molecular and cellular level. An improved understanding of a patient's tumor biology is generally expected to facilitate the personalization of treatment regimens and improve treatment outcomes.

Provided herein are methods for analyzing rare circulating cells (RCCs) in a non-enriched biological sample, including: (a) detecting RCCs in the non-enriched biological sample, including i) determining presence or absence of one or more RCC detection markers in nucleated cells in the non-enriched biological sample, and ii) assessing the morphology of the nucleated cells, wherein RCCs are detected among the nucleated cells based on a combination of distinct detection marker staining and morphological characteristics; (b) quenching the staining of the one or more RCC detection markers comprising contacting the RCCs with a quenching buffer, wherein the staining is quenched by more than 50%, 60%, 70%, 80%, 90%, 95%, 99%, 99.9% or 99.99%; and (c) analyzing the detected RCCs, comprising determining presence or absence of one or more RCC analysis probes.

Further provided herein are methods for analyzing rare circulating cells (RCCs) in a non-enriched blood sample, including: (a) detecting RCCs in the non-enriched blood sample, including i) determining presence or absence of one or more immunofluorescent RCC detection markers in nucleated cells in the non-enriched blood sample, and ii) assessing the morphology of the nucleated cells, wherein RCCs are detected among the nucleated cells based on a combination of distinct immunofluorescent staining and morphological characteristics; (b) quenching the immunofluorescence of the one or more immunofluorescent RCC detection markers comprising contacting the RCCs with a quenching buffer, wherein the immunofluorescence is quenched by more than 50%, 60%, 70%, 80%, 90%, 95%, 99%, 99.9% or 99.99%; and (c) analyzing the detected RCCs, comprising determining presence or absence of one or more fluorescent RCC analysis markers.

It must be noted that, as used in this specification and the appended claims, the term "about," particularly in reference to a given quantity, is meant to encompass deviations of plus or minus five percent.

As used in this application, including the appended claims, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

The biological samples of this disclosure can be any sample suspected to contain RCCs (e.g., CTCs, CTC candidates, CTC mimics, CECs), including solid tissue samples, such as bone marrow, and liquid samples, such as whole blood, plasma, amniotic fluid, pleural fluid, peritoneal fluid, central spinal fluid, urine, saliva and bronchial washes. In some embodiments, the biological sample is a blood sample. As will be appreciated by those skilled in the art, a biological sample can include any fraction or component of blood, without limitation, T-cells, monocytes, neutrophils, erythrocytes, platelets and microvesicles such as exosomes and exosome-like vesicles.

The biological samples of this disclosure can be obtained from any organism, including mammals such as humans, primates (e.g., monkeys, chimpanzees, orangutans, and gorillas), cats, dogs, rabbits, farm animals (e.g., cows, horses, goats, sheep, pigs), and rodents (e.g., mice, rats, hamsters, and guinea pigs).

It is noted that, as used herein, the terms "organism," "individual," "subject," or "patient" are used as synonyms and interchangeably.

The organisms of this disclosure include healthy organisms and diseased organisms.

Diseased organisms can suffer from any disease associated with aberrant RCC levels. The term "aberrant RCC levels," as used herein, refers to RCC levels in a sample that significantly deviate from the median RCC levels found in a population of healthy organisms. In some embodiments, the aberrant RCC levels are higher than the median RCC levels. In some embodiments, the aberrant RCC levels are lower than the median RCC levels.

In some embodiments, the healthy organisms have never suffered from a certain disease. In some embodiments, the healthy organisms were previously diseased. In some embodiments, the healthy organisms are undergoing a routine medical checkup. In some embodiments, the healthy organisms are members of a control group in a clinical trial. In some embodiments, the healthy organisms are at risk of contracting a disease, as determined by the presence of certain risk factors that are well known in the art. Such risk factors include, without limitation, a genetic predisposition, a personal disease history, a familial disease history, a lifestyle factor, an environmental factor, a diagnostic indicator and the like.

In some embodiments, the organism is at risk of suffering from myocardial infarction or another cardiovascular disease. In some embodiments, the organism has a genetic predisposition for developing a cardiovascular disease (e.g., resulting in high cholesterol levels, diabetes, obesity) or a family history of cardiovascular diseases. In some embodiments, the organism is subject to certain lifestyle factors promoting the development of cardiovascular disease (e.g., cigarette smoking, low exercise, high body/mass index, high fat "western" diet) or shows clinical disease manifestations of cardiovascular disease (e.g., atherosclerotic plaques, hypertension, prior medical history of the patient, chest pain, numbness in left arm). In some embodiments, the organism is a patient who is receiving a clinical workup (e.g., electrocardiogram (ECG), blood work) to diagnose a heart attack or the risk of a heart attack. In some embodiments, a heart attack is expected to be imminent (e.g., a heart attack expected to occur within one week from the time of the clinical workup). In some embodiments, the organism is a patient having elevated blood levels of troponin relative to normal controls.

In some embodiments, the organism is at risk of developing a cancer. In some embodiments, the organism has a genetic predisposition for cancer (e.g., BRCA 1 or BRCA 2 mutations) or a family history of cancer. In some embodiments, the organism was exposed to carcinogens (e.g., a cigarette smoke, exhaust fumes, smog, asbestos, environmental pollution, toxins and the like).

In some embodiments, the diseased organism suffers from a cardiovascular disease such as myocardial infarction (MI; e.g., acute myocardial infarction (MI) or stable coronary artery disease (CAD)) or stroke. In some embodiments, the diseased organism suffers from a metabolic syndrome (e.g., diabetes, obesity).

In some embodiments, the diseased organism suffers from cancer. The cancers of this disclosure typically form a solid tumor. The tumor can include a primary tumor and a metastatic tumor. The tumor can be vascularized. The cancers can be at least partly responsive to therapy (e.g., surgery, chemotherapy, radiation therapy) or unresponsive to therapy. The cancers can be resistant to one or more anti-cancer treatments (e.g., resistant to specific chemotherapy regimens). The cancers can include cancers of all stages, e.g., stage I, stage II, stage III, or stage IV cancers.

The cancers of this disclosure include, without limitation, lung cancer (e.g., small-cell lung cancer (SCLC), non-small cell lung cancer (NSCLC), including, e.g., adenocarcinomas or lung carcinoid tumor), skin cancer, colon cancer, renal cancer, liver cancer, pancreatic cancer, thyroid cancer, bladder cancer, gall bladder cancer, brain cancer (e.g., glioma, glioblastoma, medulloblastoma, neuroblastoma), breast cancer, ovarian cancer, endometrial cancer, prostate cancer, testicular cancer and lymphomas (e.g., Hodgkin's lymphoma, non-Hodgkin's lymphoma, T-cell lymphoma, B-cell lymphoma).

In some embodiments, the diseased organism is treatment naïve. In some embodiments, the diseased organism has received a treatment prior to sample collection. In some embodiments the diseased organism is undergoing treatment at the time of sample collection. Treatments can include, without limitation, drug treatments, radiation treatments, surgery, and the like.

In some embodiments, the treatment includes a drug treatment (e.g., beta blockers, anti-coagulants (e.g., aspirin, plavix), nitro, heparin, morphine, statins, insulin, chemotherapy, VEGF antagonists, EGFR antagonists, HER2 antagonists, kinase inhibitors). In some embodiments, the treatment includes surgery (e.g., endarterectomy, tumor excision). In some embodiments, the treatment includes radiation therapy. In some embodiments, the treatment includes a combination of treatements (e.g., a combination of two or more drug treatments, a combination of a drug treatment with a radiation treatment).

In some embodiments, the organism is an animal model. In some embodiments, the organism is an animal model for a cardiovascular disease. In some embodiments, the organism is an animal model for cancer, including, without limitation, a xenograft mouse model, a transgenic mouse carrying a transgenic oncogene, a knockout mouse lacking a proapoptotic gene and others. A person of ordinary skill understands that animal models (in mice or other organisms) are well known in the art for a series of disease conditions.

In some embodiments, the blood sample was obtained from a patient. In some embodiments, the patient received a treatment for a period of time (e.g., for more than 1 day, 1 week, 1 month, 3 months, 6 months, 9 months, 1 year, 2 years, 3 years, 4 years, 5 years). In some embodiments the blood sample is a plurality of blood samples. In some embodiments the plurality of blood samples were collected over a period of time. In some embodiments, at least one blood sample of the plurality of blood samples was collected before the patient received a treatment for a period of time.

In some embodiments, at least one blood sample of the plurality of blood samples was obtained when the patient was treatment naïve. In some embodiments, at least one blood sample of the plurality of blood samples was obtained from a patient during the period of time when the patient received a treatment. In some embodiments, at least one blood sample of the plurality of blood samples was obtained before the patient received a treatment for a period of time and at least one blood sample of the plurality of blood samples was obtained during the period of time when the received the treatment. In some embodiments, a first blood sample was obtained at a first time during the period of time when the patient received a treatment and a second blood sample was obtained at a second time during the period of time when the patient received the treatment. In some embodiments the first time and the second time were separated by a period of time of more than 1 day, 1 week, 2 weeks, 1 month, 2 months, 3 months, 6 months, 9 months, 1 year, 2 years, 3 years, 4 years or 5 years.

In some embodiments, the blood sample was obtained from a non-small cell lung cancer (NSCLC) patient. In some embodiments, the blood sample was obtained from a MI patient.

In some embodiments, the methods further include the initial step of obtaining a blood sample from a patient.

The samples of this disclosure can each contain a plurality of cell populations and cell subpopulation that are distinguishable by methods well known in the art (e.g., FACS, immunohistochemistry). For example, a blood sample can contain populations of non-nucleated cells, such as erythrocytes (e.g., 4-5 million/µl) or platelets (150,000-400,000 cells/µl), and populations of nucleated cells such as white blood cells (WBCs, e.g., 4,500-10,000 cells/µl), CECs or CTCs (circulating tumor cells; e.g., 2-800 cells/µl). WBCs can contain cellular subpopulations of, e.g., neutrophils (2,500-8,000 cells/µl), lymphocytes (1,000-4,000 cells/µl), monocytes (100-700 cells/µl), eosinophils (50-500 cells/µl), basophils (25-100 cells/µl) and the like. The samples of this disclosure are non-enriched samples, i.e., they are not enriched for any specific population or subpopulation of nucleated cells. For example, non-enriched blood samples are not enriched for any WBCs, B-cells, T-cells, NK-cells, monocytes, or the like. Specifically, the blood samples of this disclosure are not enriched for any RCC, including CTCs, CTC mimics, CECs or the like.

The samples of this disclosure can be obtained by any applicable method known to a person of skill, including, e.g., by solid tissue biopsy or by fluid biopsy (see, e.g., Marrinucci D. et al., 2012, Phys. Biol. 9 016003; Nieva J. et al., 2012, Phys. Biol. 9 016004). A blood sample can be extracted from any source known to include blood cells or components thereof, such as venous, arterial, peripheral, tissue, cord and the like. The sample can be processed using well known and routine clinical methods (e.g., procedures for drawing and processing whole blood). In some embodiments, a blood sample is drawn into anti-coagulant blood collection tubes (BCT), which can contain EDTA or Streck Cell-Free DNA™. In other embodiments, a blood sample is drawn into CellSave® tubes (Veridex). A blood sample can be stored for up to 12 hours, 24 hours, 36 hours, 48 hours, 60 hours, 72 hours, 86 hours, 96 hours, 108 hours or 120 hours or longer before further processing.

In some embodiments, the methods of this disclosure comprise obtaining a white blood cell (WBC) count for the blood sample. In certain embodiments, the WBC count may be obtained by using a HemoCure® WBC device (Hemocure, Ängelholm, Sweden).

In some embodiments, the methods of this disclosure comprise a step of lysing erythrocytes in the blood sample. In some embodiments, the erythrocytes are lysed, e.g., by adding an ammonium chloride solution to the blood sample. In certain embodiments, a blood sample is subjected to centrifugation following erythrocyte lysis and nucleated cells are resuspended, e.g., in a PBS solution.

In some embodiments, nucleated cells from a sample, such as a blood sample, are deposited as a monolayer on a planar support. The planar support can be of any material, e.g., any fluorescently clear material, any material conducive to cell attachment, any material conducive to the easy removal of cell debris, any material having a thickness of <100 µm. In some embodiments, the material is a film. In some embodiments the material is a glass slide. The glass slide can be coated to allow maximal retention of live cells (See, e.g., Marrinucci D. et al., 2012, Phys. Biol. 9 016003). In some embodiments, about 0.5 million, 1 million, 1.5 million, 2 million, 2.5 million, 3 million, 3.5 million, 4 million, 4.5 million, or 5 million nucleated cells are deposited onto the glass slide. In some embodiments, the methods of this disclosure comprise an initial step of depositing nucleated cells from the blood sample as a monolayer on a glass slide. In certain embodiments, the method comprises depositing about 3 million cells onto a glass slide. In some embodiments, the WBC count is used to determine the amount of blood required to plate a consistent loading volume of nucleated cells per glass slide.

In some embodiments, the methods of this disclosure comprise an initial step of identifying nucleated cells in the non-enriched blood sample. In some embodiments, the nucleated cells are identified with a fluorescent stain. In certain embodiments, the fluorescent stain comprises a nucleic acid specific stain. In certain embodiments, the fluorescent stain is diamidino-2-phenylindole (DAPI).

The term "rare cell", as used herein, refers to a cell that has an abundance of less than 1:1,000 in a cell population, e.g., an abundance of less than 1:5,000, 1:10,000, 1:30,000, 1:50:000, 1:100,000, 1:300,000, 1:500,000, or 1:1,000,000. In some embodiments, the rare cell has an abundance of 1:50:000 to 1:100,000 in the cell population.

The term "sample cell", as used herein, refers to any cell in a sample that is not a rare cell. For example, sample cells in a blood sample include WBCs.

In some embodiments, the rare cells of this disclosure are rare circulating cells (RCCs). In some embodiments, the RCCs are circulating in the blood stream of an organism. In some embodiments, the RCC is a circulating tumor cell (CTC). In some embodiments, the RCC is a circulating epithelial cell (CEC). In some embodiments, the RCC is a CTC mimic. In some embodiments, the RCC is a CTC candidate.

The Circulating Tumor Cells (CTCs) of this disclosure are tumor cells that are circulating in the bloodstream of an organism.

The Circulating Endothelial Cells (CECs) of this disclosure are endothelial cells that are circulating in the bloodstream of an organism.

The term "CTC mimic", as used herein, refers to a cell that, while sharing one or more biomarkers, morphological characteristics, or a combination thereof, with a CTC, is not a CTC. In some embodiments, a CTC mimic is a CEC.

The term "CTC candidate", as used herein, refers to a cell that is detected based on the presence of a biomarker or a morphological characteristic, or combination thereof, that is shared between CTC mimics and CTCs. A CTC candidate can be a CTC or a CTC mimic. A CTC candidate can be identified as a CTC or a CTC mimic based on the detection of further biomarkers, further morphological characteristics, or combinations thereof that are characteristic of a CTC or another RCC.

The RCCs of this disclosure are detected among the nucleated cells of a sample based on a combination of distinct biomarkers and morphological characteristics.

The term "CEC detection marker", as used herein, refers to a biomarker that can be used to detect CECs, but not certain other RCCs (e.g., CTCs) or certain sample cells (e.g., WBCs). In some embodiments, the CEC marker is present in CECs, CTC mimics and CTC candidates and absent in CTCs and WBCs.

CEC detection markers include, without limitation, any biomarker that is specific for endothelial cells (e.g., cluster of differentiation (CD) 146, Von Willebrand factor (vWF), CD 31, CD 34, or CD 105).

The term "CTC detection marker", as used herein, refers to a biomarker that can be used to detect CTCs, but not certain other RCCs (e.g., CECs) or certain sample cells (e.g., WBCs). In some embodiments, the CTC detection marker is present in CTCs, CTC candidates and CTC mimics and absent in CECs and WBCs.

CTC detection markers include, without limitation, any cancer-specific biomarker. Cancer-specific biomarkers can include, for example, biomarkers that are specific for a given cancer-type of interest (e.g., non-small cell lung cancer, NSCLC), a clinical cancer-stage of interest (e.g., stage IV), or a cancer cell property of interest (e.g., energy metabolism, epithelial-mesenchymal transition). Additionally, cancer-specific biomarkers can include more general cancer markers, such as cancer markers that are present in several cancer-types, but not in normal cells, or cancer markers that generally signal the malignant transformation of a cell. A person of skill will recognize that many specific and general cancer-specific biomarkers are known in the art.

CTC detection markers include, without limitation, anaplastic lymphoma kinase (ALK), androgen receptor (AR), Axl, cMET, cytokeratins 1, 4, 5, 6, 7, 8, 10, 13, 18 or 19; CD 31, CD 99, CD 117, chromatogranin, desmin, E-cadherin, epidermal growth factor receptor (EGFR), epithelial cell adhesion molecule (EpCAM), epithelial membrane antigen (EMA), gross cystic disease fluid protein (GCDFP-15), HMB-45, inhibin, MART-1, MCM2, Myo D1, muscle-specific actin (MSA), N-cadherin, neurofilament, neuron-specific enolase (NSE), p63, placental alkaline phosphatase (PLAP), prostate specific membrane antigen (PSMA), S100 protein, smooth muscle actin (SMA), synaptophysin, thyroid transcription factor-1 (TTF-1), tumor M2-PK (i.e., pyruvate kinase isoenzyme type M2), vimentin and more.

The term "RCC detection marker", as used herein, refers to a biomarker that is present in a RCC of interest, but not in a sample cell. In some embodiments, the RCC marker is present in one type of RCCs (e.g., a CEC marker that is only present in CECs). In some embodiments, the RCC marker is present in more than one type of RCCs (e.g., a CTC marker that is present in CTCs and CTC mimics). The RCC detection markers of this disclosure can be used to detect RCCs, but not sample cells, such as WBCs. RCC detection markers include, for example, CTC markers, CEC markers and the like.

The term "sample cell detection marker", as used herein, refers to any biomarker that is present in at least one sample cell, but that is not present in an RCC of interest. In some embodiments, the sample cell detection marker is present in at least one cell-type in the sample and absent in CECs, CTCs, CTC candidates and CTC mimics. The sample cell detection markers of this disclosure are present in a sample cell that is more abundant than CECs, CTCs, CTC candidates, or CTC mimics. In some embodiments, the sample cell detection marker is present in a WBC and absent in CECs, CTCs, CTC candidates and CTC mimics. In some embodiments, the sample cell detection marker is CD 45. In some embodiments the methods include determining presence or absence of a sample cell detection marker.

The term "biomarker," as used herein, refers to a biological molecule, or a fragment of a biological molecule, the change and/or the detection of which can be correlated with the identity of an RCC or with a particular physical condition or state of an RCC. In some embodiments, the biomarkers are detection markers. In some embodiments, the biomarkers are analysis markers.

The term "detection marker", as used herein, refers to a biomarker that is used to identify a cell as belonging to a certain cell-type of interest, e.g., a CTC, CEC or WBC. Detection markers can be used to differentiate one cell type from another cell type (e.g., differentiate a CTC mimic from a CTC). Generally, the detection markers of this disclosure can be used for cell identification, classification, and quantification.

The term "analysis marker" as used herein, refers to a biomarker that is used to describe a cell with respect to a cell biological or molecular biological property of interest. For example, without limitation, analysis markers can describe certain aspects of a cellular genome (e.g., gene mutations (e.g., oncogene mutations), gene amplifications), transcriptome (gene expression profiles), proteome (protein expression profiles, post-translational protein modifications, intracellular protein localization), secretome, metabolome (metabolic activity, including energy metabolism), lipidome (lipid profiles, lipid rafts) and the like.

The terms "marker" and "biomarker" are used interchangeably throughout the disclosure. Such biomarkers include, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term also encompasses portions or fragments of a biological molecule, for example, peptide fragment of a protein or polypeptide. In some embodiments, biomarkers (e.g., RCC analysis markers) are disease marker (e.g., oncogenic mutations). In some embodiments, biomarkers (e.g., RCC analysis markers) are used to distinguish and identify subpopulations of cells.

A person skilled in the art will appreciate that a number of methods can be used to determine the presence or absence of a biomarker, including microscopy based approaches, such as fluorescence microscopy or fluorescence scanning microscopy (see, e.g., Marrinucci D. et al., 2012, Phys. Biol. 9 016003; Nieva J. et al., 2012, Phys. Biol. 9 016004). Other approaches include mass spectrometry, gene expression analysis (e.g., gene-chips, Southern Blots, PCR, FISH) and antibody-based approaches, including immunofluorescence, immunohistochemistry, immunoassays (e.g., Western blots, enzyme-linked immunosorbent assay (ELISA), immunoprecipitation, radioimmunoassay, dot blotting, and FACS). In some embodiments, the methods of this disclosure are performed in an automated or robotic fashion. In some embodiments, the signals from multiple samples are detected simultaneously.

A person of skill in the art will further appreciate that the presence or absence of biomarkers in a cell can be detected using any class of marker-specific binding reagents known in the art, including, e.g., antibodies, aptamers, fusion proteins, such as fusion proteins including protein receptor or protein ligand components (e.g. CD 146, vWF, CD 31, CD 34, CD 105, or CD 45-binding receptors or ligands), biomarker-specific peptides, small molecule binders or nucleic acids (e.g., antisense oligonucleotides, hybridization probes).

In some embodiments, the presence or absence of vWF, CD 146, CD31, CD 34, CD 105, CD 45 or a cytokeratin (e.g., cytokeratin 1, 4, 5, 6, 7, 8, 10, 13, 18 or 19), or a combination thereof, is determined by an antibody. In some embodiments, the presence or absence of vWF and one or more cytokeratins (e.g., cytokeratin 1, 4, 5, 6, 7, 8, 10, 13, 18 or 19) is determined by antibodies. In some embodiments, the presence or absence of vWF, one or more cytokeratin (e.g., cytokeratin 1, 4, 5, 6, 7, 8, 10, 13, 18 or 19) or CD 45 is determined by antibodies.

The antibodies of this disclosure bind specifically to a biomarker. In some embodiments, the antibodies bind specifically to a single biomarker (e.g., cytokeratin 1). In other embodiments, the antibodies are pan-specific. Pan-specific antibodies of this disclosure can bind specifically to one or more members of a biomarker family (e.g., one or more members of the cytokeratin family, including cytokeratins 1, 4, 5, 6, 7, 8, 10, 13, 18 and 19). The antibody can be any immunoglobulin or derivative thereof, whether natural or wholly or partially synthetically produced. All antibody derivatives which maintain specific binding ability can also be used. The antibody has a binding domain that is homologous or largely homologous to an immunoglobulin binding domain and can be derived from natural sources, or partly or wholly synthetically produced. The antibody can be a monoclonal or polyclonal antibody. In some embodiments, the antibody is a single-chain antibody. In some embodiments, the antibody includes a single-chain antibody fragment. In some embodiments, the antibody can be an antibody fragment including, but not limited to, Fab, Fab', F(ab')2, scFv, Fv, dsFv diabody, and Fd fragments. Due to their smaller size antibody fragments can offer advantages over intact antibodies in certain applications. Alternatively or additionally, the antibody can comprise multiple chains which are linked together, for example, by disulfide linkages, and any functional fragments obtained from such molecules, wherein such fragments retain specific-binding properties of the parent antibody molecule. Those of ordinary skill in the art will appreciate that the antibody can be provided in any of a variety of forms including, for example, humanized, partially humanized, chimeric, chimeric humanized, etc. The antibody can be prepared using any suitable methods known in the art. For example, the antibody can be enzymatically or chemically produced by fragmentation of an intact antibody or it can be recombinantly produced from a gene encoding the partial antibody sequence.

A wide variety of detectable labels can be used for the direct or indirect detection of biomarkers. Suitable detectable labels include, but are not limited to, fluorescent dyes (e.g., fluorescein, fluorescein isothiocyanate (FITC), Oregon Green™, rhodamine, Texas Red, tetrarhodamine isothiocynate (TRITC), Cy3, Cy5, Alexa Fluor® 647, Alexa Fluor® 555, Alexa Fluor® 488), fluorescent protein markers (e.g., green fluorescent protein (GFP), phycoerythrin, etc.), enzymes (e.g., luciferase, horseradish peroxidase, alkaline phosphatase, etc.), nanoparticles, biotin, digoxigenin, metals, and the like.

In some embodiments, the biomarkers are fluorescent markers. In some embodiments, the biomarkers are immunofluorescent markers. In some embodiments, the biomarkers are fluorescence in situ hybridization (FISH) markers.

In some embodiments, the immunofluorescent markers are immunofluorescent analysis markers. In some embodiments, the immunofluorescent markers are immunofluorescent detection markers. In some embodiments, the immunofluorescent detection markers are immunofluorescent RCC detection markers. In some embodiments, the immunofluorescent RCC detection markers are immunofluorescent CTC detection markers. In some embodiments, the immunofluorescent RCC detection markers are immunofluorescent CEC detection markers.

In some embodiments, the immunofluorescent CTC detection markers include a cytokeratin (CK). Cytokeratins include, e.g., cytokeratin 1, 4, 5, 6, 7, 8, 10, 13, 18 or 19. In some embodiments, the immunofluorescent CTC detection marker is a plurality of cytokeratins, including two or more of cytokeratins 1, 4, 5, 6, 7, 8, 10, 13, 18 or 19.

In some embodiments, the immunofluorescent CEC detection markers include Von Willebrand factor (vWF), cluster of differentiation (CD) 31, CD 34, CD 105, CD 145 or CD 146.

In some cells the sample cell markers are immunofluorescent sample cell markers. In some embodiments, the immunofluorescent sample cell markers are specific for white blood cells (WBCs). In certain embodiments the immunofluorescent sample cell markers comprise CD 45. In some embodiments, the methods include determining presence or absence or one or more immunofluorescent sample cell detection markers in the nucleated cells.

In some embodiments, the distinct immunofluorescent staining of nucleated cells of a sample includes the presence or absence of immunofluorescent detection markers, such as immunofluorescent RCC detection markers.

In some embodiments, the distinct immunofluorescent staining of CTCs includes the presence of an immunofluorescent CTC detection marker, the absence of an immunofluorescent CEC detection marker, and the absence of an immunofluorescent sample cell detection marker. In some embodiments, the distinct immunofluorescent staining of CTCs includes positive staining for CK, negative staining for vWF and negative staining for CD45 ($CK^+/vWF^-/CD45^-$).

In some embodiments, the distinct immunofluorescent staining of CECs includes the presence of an immunofluorescent CEC detection marker, the absence of an immunofluorescent CTC detection marker and the absence of an immunofluorescent sample cell detection marker. In some embodiments, the distinct immunofluorescent staining of CECs includes positive staining for vWF, negative staining for CK and negative staining for CD45 ($vWF^+/CK^-/CD45^-$).

In some embodiments, the distinct immunofluorescent staining of CTC mimics includes the presence of an immunofluorescent CTC detection marker, the presence of an immunofluorescent CEC detection marker, and the absence of an immunofluorescent sample cell detection marker. In some embodiments, the distinct immunofluorescent staining of CTC mimics includes positive staining for CK, positive staining for vWF and negative staining for CD45 ($CK^+/vWF^+/CD45^-$).

In some embodiments, the distinct immunofluorescent staining of CTC candidates includes the presence of an immunofluorescent CTC detection marker, the absence of an immunofluorescent CEC detection marker, and the absence of an immunofluorescent sample cell detection marker. In other embodiments, the distinct staining of CTC candidates includes the presence of an immunofluorescent CTC detection marker, the presence of an immunofluorescent CEC detection marker, and the absence of an immunofluorescent sample cell detection marker. In some embodiments, the distinct immunofluorescent staining of CTC candidates includes positive staining for CK and negative staining for CD45 ($CK^+/CD45$).

In some embodiments, the distinct immunofluorescent staining of a sample cell includes the presence of an immunofluorescent sample cell detection marker, the absence of an immunofluorescent CEC detection marker and the absence of an immunofluorescent CTC detection marker.

In some embodiments, the distinct immunofluorescent staining of a CEC, CTC, CTC mimic, CTC candidate or sample cell includes distinct intracellular staining patterns for an immunofluorescent CEC detection marker, an immunofluorescent CTC detection marker, or an immunofluorescent sample cell detection marker. For example, the intracellular staining for an immunofluorescent marker of this disclosure can be distinctly diffuse, punctuate, cytoplasmic, nuclear or membrane bound.

In some embodiments, determining presence or absence of an immunofluorescent RCC detection marker comprises comparing the distinct immunofluorescent staining of RCCs with the distinct immunofluorescent staining of WBCs.

In some embodiments, determining presence or absence of an immunofluorescent CTC detection marker includes comparing the distinct immunofluorescent staining of CTC candidates with the distinct immunofluorescent staining of a sample cell. In some embodiments, determining presence or absence of an immunofluorescent CTC detection marker includes comparing the distinct immunofluorescent staining of CTC candidates with the distinct immunofluorescent staining of WBCs.

In some embodiments, determining presence or absence of an immunofluorescent CEC detection marker includes comparing the distinct immunofluorescent staining of CEC candidates with the distinct immunofluorescent staining of a sample cell. In some embodiments, determining the presence or absence of an immunofluorescent CEC detection marker includes comparing the distinct immunofluorescent staining of CTC candidates with the distinct immunofluorescent staining of WBCs.

In some embodiments, the morphological characteristics include nucleus size, nucleus shape, cell size, cell shape, and nuclear-to-cytoplasmic ratio. In some embodiments, assessing the morphology of RCCs includes assessing the RCCs by nuclear detail, nuclear contour, presence or absence of nucleoli, quality of cytoplasm, quantity of cytoplasm, or immunofluorescent staining patterns. In some embodiments, the method further comprises assessing the aggregation characteristics of RCCs.

A person of ordinary skill in the art understands that the morphological characteristics of this disclosure can include any feature, property, characteristic or aspect of a cell that can be determined and correlated with the detection of RCCs.

The methods of this disclosure can be performed with any microscopic method known in the art. In some embodiments, the method is performed by fluorescent scanning microscopy. In some embodiments the microscopic method provides high-resolution images of RCCs and their surrounding WBCs (see, e.g., Marrinucci D. et al., 2012, Phys. Biol. 9 016003; Nieva J. et al., 2012, Phys. Biol. 9 016004). In some embodiments, a slide coated with a monolayer of nucleated cells from a sample, such as a non-enriched blood sample, is scanned by a fluorescent scanning microscope and the fluorescence intensities from immunofluorescent detection markers and nuclear stains are recorded. The scanned images are analyzed to determine the presence or absence of immunofluorescent detection markers and to assess the morphology of the nucleated cells, including RCCs. In some embodiments, microscopic data collection and analysis is conducted in an automated manner.

In some embodiments, the microscopic field contains RCCs and WBCs. In some embodiments, the microscopic field shows at least 1, 5, 10, 20, 50, or 100 RCCs. In some embodiments, the microscopic field shows at least 10, 25, 50, 100, 250, 500, or 1,000 fold more WBCs than RCCs. In certain embodiments, the microscopic field shows RCCs, wherein each RCC is surrounded by at least 10, 50, 100, 150, 200, 250, 500, 1,000 or more WBCs.

In certain embodiments, the microscopy provides a field of view comprising more than 2, 5, 10, 20, 30, 40 or 50 RCCs, wherein each RCC is surrounded by more than 10, 50, 100, 150 or 200 WBCs. In some embodiments, the microscopy provides a field of view comprising more than 10 RCCs, wherein each RCC is surrounded by more than 200 WBCs.

In some embodiments, a biomarker is considered "present" in a cell if it is detectable above the background signal and noise of the respective detection method used (e.g., 2-fold, 3-fold, 5-fold, or 10-fold higher than the background; $2\sigma$ or $3\sigma$ over background). In some embodiments, a biomarker is considered "absent" if it is not detectable above the background noise of the detection method used (e.g., <1.5-fold or <2.0-fold higher than the background signal; <$1.5\sigma$ or <$2.0\sigma$ over background).

In some embodiments, the presence or absence of immunofluorescent markers in nucleated cells is determined by selecting the exposure times during the fluorescence scanning process such that all immunofluorescent markers achieve a pre-set level of fluorescence on the WBCs in the field of view. Under these conditions, immunofluorescent RCC detection markers, for example, are visible on the WBCs as background signals with fixed heights, even though the respective immunofluorescent RCC detection markers are not present in WBCs. Moreover, WBC-specific immunofluorescent sample cell detection markers are visible on RCCs as background signals with fixed heights, even though the markers are not present in RCCs.

A cell is considered positive for an immunofluorescent marker (i.e., the marker is considered present) if its fluorescent signal for the respective marker is significantly higher than the fixed background signal (e.g., 2-fold, 3-fold, 5-fold, or 10-fold higher than the background; $2\sigma$ or $3\sigma$ over background). For example, a nucleated cell is considered CD 45-positive (CD $45^+$) if its fluorescent signal for CD 45 is significantly higher than the background signal. A cell is considered negative for an immunofluorescent marker (i.e., the marker is considered absent) if the cell's fluorescence signal for the respective marker is not significantly higher than the background signal or noise (e.g., <1.5-fold or <2.0-fold higher than the background signal; e.g., <$1.5\sigma$ or <$2.0\sigma$ over background).

The relative expression levels of an immunofluorescent RCC detection marker can be expressed by comparing the fluorescence signal of a cell that is positive for the respective marker (i.e., a CTC, CTC candidate, CTC mimic or CEC) with the corresponding fluorescence signal of surrounding cells that are negative for the immunofluorescent RCC detection marker (e.g., a WBC). For example, the relative expression of the CTC marker cytokeratin on a given CTC candidate is >5 if the fluorescence signal for cytokeratin on the cell is >5-fold higher than, e.g., the average or median fluorescence signal of surrounding WBCs.

A cell is considered a nucleated cell if it shows a fluorescence signal for a nuclear stain (e.g., DAPI) that is significantly higher than the background signal or noise, e.g., as detected for a non-nucleated platelet cell or for representative cell-free areas on a microscope slide.

In some embodiments, determining the presence of an immunofluorescent CTC detection marker in nucleated cells includes identifying nucleated cells having a relative expression of the CTC detection marker of >2, >3, >4, >5, >6, >7, >8, >9 or >10. In some embodiments, determining the presence of CK in nucleated cells includes identifying nucleated cells having a relative CK expression of >3.

In some embodiments, determining the presence of an immunofluorescent CEC detection marker in CTC candidates includes identifying CTC candidates having a relative expression of the CEC detection marker of >2, >3, >4, >5, >6, >7, >8, >9 or >10. In some embodiments, determining the presence of vWF in CTC candidate includes identifying CTC candidate cells having a relative vWF expression of >6.

In some embodiments, the morphological assessment of a nucleated cell, such as the determination of its size or shape, is based on the fluorescence signals of an immunofluorescent detection marker (see, e.g., Marrinucci D. et al., 2012, Phys. Biol. 9 016003; Nieva J. et al., 2012, Phys. Biol. 9 016004).

In some embodiments, the RCCs are morphologically distinct from the surrounding nucleated cells, such as WBCs. In some embodiments, assessing the morphology of the nucleated cells comprises comparing the morphological characteristics of the RCC with the morphological characteristics of surrounding WBCs.

In some embodiments, the CTCs, CTC mimics, CTC candidates and CECs are morphologically distinct from the surrounding WBCs. In some embodiments, assessing the morphology of the CTC candidate comprises comparing the morphological characteristics of the CTC candidate with the morphological characteristics of surrounding WBCs.

In some embodiments, the CTCs, CTC mimics, CTC candidates and CECs are morphologically distinct from each other. In some embodiments, assessing the morphology of the CTC candidate comprises comparing the morphological characteristics of the CTC candidate with the morphological characteristics of a CTC. In some embodiments, assessing the morphology of the CTC candidate comprises comparing the morphological characteristics of the CTC candidate with the morphological characteristics of a CEC.

Morphological features shared between CTCs and CTC mimics include, for example and without limitation, the presence of distinct and intact nuclei, the presence of nuclei with irregular shapes, the presence of condensed chromatin, a nuclear area that is larger than the nuclear area of WBCs, a cytoplasmic area that is larger than the cytoplasmic area of WBCs, a higher cytoplasmic-to-nuclear ratio relative to WBCs, the presence of aggregates of two or more cytokeratin positive ($CK^+$) cells, or combinations thereof.

Morphological features shared between CECs and CTC mimics include, for example and without limitation, the presence of nuclei with irregular shapes, the presence of elongated nuclei, the presence of an elongated cytoplasm, a nuclear area that is larger than the nuclear area of WBCs, a cytoplasmic area that is larger than the cytoplasmic area of WBCs, a higher cytoplasmic-to-nuclear ratio relative to WBCs, the presence of aggregates of two or more cytokeratin positive ($vWF^+$) cells, or combination thereof.

In some embodiments, the (average or mean) nuclear area of RCCs in a microscopic field of view is at least 5%, 10%, 15%, 20%, 25%, 30%, 35%, 40%, 45% or 50% greater than the nuclear area of WBCs.

In some embodiments, the (average or mean) cytoplasmic area of RCCs in a microscopic field of view is at least 5%, 10%, 15%, 20%, 25%, 30%, 35%, 40%, 45% or 50% greater than the cytoplasmic area of WBCs.

In some embodiments, the (average or mean) cytoplasmic-to-nuclear ratio of RCCs in a microscopic field of view is at least 5%, 10%, 15%, 20%, 25%, 30%, 35%, 40%, 45% or 50% greater than the cytoplasmic-to-nuclear ratio of WBCs.

In some embodiments (also referred to as "high-definition (HD)"-RCC Assay), the comparison of an RCC (i.e., a target cells of interest) with surrounding WBCs (i.e., negative control cells) improves the performance of the method, e.g., by increasing the accuracy, specificity, or sensitivity of the method, relative to a method wherein no such comparison is performed. In some embodiments, RCCs are compared with surrounding WBCs when determining the presence or absence of an immunofluorescent RCC detection marker. In some embodiments, RCCs are compared with surrounding WBCs when assessing the morphology of nucleated cells. In some embodiments, RCCs are compared with surrounding WBCs when determining the presence or absence of an immunofluorescent RCC detection marker and when assessing the morphology of nucleated cells.

In some embodiments, assessing the morphology of the nucleated cells includes assessing the morphology of RCC aggregates. In some embodiments, assessing the morphology of RCC aggregates includes quantifying the RCC aggregates in the blood sample. In some embodiments, assessing the morphology of RCC aggregates includes assessing the percent of detected RCCs that are in an aggregated from. In some embodiments, assessing the morphology of RCC aggregates includes quantifying the average or mean number of cells per aggregate in a sample.

In some embodiments, the methods are used to calculate the concentration of RCCs in a sample (e.g., in [RCC/ml]). For example, CTCs are detected in a human blood sample according to the methods of this disclosure. Next, the ratio of CTCs to total nucleated cells (i.e., CTCs, CTC candidates, CTC mimics, CECs plus sample cells, such as WBCs) is determined for a field of vision. Then, the CTC mimic/total nuclear cell ratio is multiplied by the concentration of total nucleated cells in a blood sample (e.g., as determined using a standard automated cell counter) to calculate the concentration of CTC mimics in the blood sample.

According to the methods of this disclosure, the RCCs can be further analyzed after they were detected, and optionally quantified, by a method of this disclosure.

In some embodiments, the methods of this disclosure include quenching the staining of the one or more RCC detection markers comprising contacting the RCCs with a quenching buffer, wherein the staining is quenched by more than 50%, 55%, 60%, 65%, 70%, 75%, 80%, 85%, 90%, 95% or 99%.

In some embodiments, the methods of this disclosure include quenching the immunofluorescence of the one or more immunofluorescent RCC detection markers comprising contacting the RCCs with a quenching buffer, wherein the immunofluorescence is quenched by more than 50%, 55%, 60%, 65%, 70%, 75%, 80%, 85%, 90%, 95% or 99%.

In some embodiments, the quenching buffer contains a chaotropic agent. The term "chaotropic agent", as used herein, refers to a substance that can disrupt the secondary or tertiary structure of biological macromolecules, such as proteins and nucleic acids (e.g., DNA, RNA) or dissolve lipid bilayers, such as plasma membranes. Chaotropic agents include, without limitation, chaotropic salts (e.g., guanidinium chloride (guanidine chloride), lithium perchlorate, lithium acetate, magnesium chloride, sodium dodecyl sulfate), chaotropic solvents (e.g., butanol, ethanol), or uncharged, solid chaotropes (e.g., urea, thiourea).

In some embodiments the concentration of the chaotropic agent is less than 10 M, less than 8 M, less than 6 M, less than 4 M, less than 2 M, less than 1 M, or less than 0.5 M. In some embodiments, the concentration of the chaotropic agent is at least 0.5M, at least 1 M, at least 2M, at least 4M, at least 6M or at least 8M.

In some embodiments, the quenching buffer contains a chaotrophic salt. In some embodiments, the quenching buffer contains guanidine or a guanidine salt. In some embodiments, the quenching buffer contains guanidinium thiocyanate (guanidine thiocyanate) or guanidinium chloride (guanidine hydrochloride).

In some embodiments, the RCCs are contacted with the quenching buffer for a period of time of more than 1 minute, more than 2 minutes, more than 3 minutes, more than 4 minutes, more than 5 minutes, more than 6 minutes, more than 7 minutes, more than 8 minutes, more than 9 minutes, more than 10 minutes, more than 15 minutes or more than 20 minutes. In some embodiments, the RCCs are contacted with the quenching buffer for a period of time of less than 1 minute, less than 45 seconds, less than 30 seconds, less than 15 seconds, less than 10 second or less than 5 seconds.

In some embodiments, the RCCs are contacted with the quenching buffer at a temperature of less than 37° C., less than 34° C., less than 30° C., less than 25° C., less than 20° C., less than 15° C., less than 10° C., less than 5° C., or less than 1° C. In some embodiments, RCCs are contacted with the quenching buffer at a temperature of about 4° C.

In some embodiments, the RCCs are detected in a non-enriched blood sample placed on a solid support (e.g., on a glass slide). In some embodiments, a certain fraction of RCCs detected in the HD-RCC assay is washed off the solid support during incubation with the quenching buffer. These cells are physically unavailable for further analysis.

In some embodiments, more than 50%, more than 55%, more than 60%, more than 65%, more than 70%, more than 75%, more than 80%, more than 85%, more than 90%, more than 95% or more than 99% of detected RCCs that were present on the solid support prior to incubation with quenching buffer are retained on the solid support after incubation with quenching buffer.

In some embodiments, more than 50%, more than 55%, more than 60%, more than 65%, more than 70%, more than 75%, more than 80%, more than 85%, more than 90%, more than 95% or more than 99% of RCCs that were detected in the blood sample by a method of this disclosure are physically present for further analysis after incubation with quenching buffer.

In some embodiments, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 99% of RCCs detected in (a) in a method of this disclosure are retained in (c) in a method of this disclosure.

In some embodiments, the methods include analyzing the detected RCCs by determining presence or absence of one or more fluorescent RCC analysis markers. In some embodiments, the RCC analysis markers are present in more than 25%, more than 30%, more than 35%, more than 40%, more than 45%, more than 50%, more than 55%, more than 60%, more than 65%, more than 70%, more than 75%, more than 80%, more than 85%, more than 90%, more than 95% or more than 99% of RCCs analyzed in (c) in a method of this disclosure.

In some embodiments, determining presence or absence of the fluorescent RCC analysis markers includes comparing the distinct fluorescent staining of RCCs with the distinct fluorescent staining of WBCs.

The RCC analysis marker can include any molecular probe that indicates the cell biological or molecular biological status of an RCC. The cell biological or molecular biological status of an RCC can include, without limitation, cell morphological characteristics, cellular dynamics (e.g., cell motility, adhesion to extracellular matrix substrates), intracellular localization or structural characteristics (e.g., intracellular localization of organelles, biomolecules; formation and localization of biomolecular assemblies, such as lipid rafts), metabolic characteristics (e.g., energy metabolism, intracellular signaling), genomic characteristics (e.g., gene expression, gene mutations, mRNA splicing) or proteomic characteristics (protein expression, localization, post-translational modification, secretome profile).

In some embodiments, the RCC analysis marker includes a genetic mutation (e.g., a gene deletion, duplication, amplification, translocation, point-mutation). In some embodiments, the RCC analysis marker includes the elevated expression of a gene of interest (e.g., an oncogene). In some embodiments, the RCC analysis marker includes the reduced expression of a gene of interest (e.g., a tumor suppressor gene). In some embodiments, the RCC analysis marker includes the elevated expression of an mRNA of interest. In some embodiments, the RCC analysis marker includes the elevated expression of a protein of interest (e.g., HER2, Bcl-2). In some embodiments, the RCC analysis marker includes a specific intracellular localization of a protein of interest (e.g., nuclear localization, cytoplasmic localization). In some embodiments, the RCC analysis marker includes a post-translational protein modification (e.g., phosphorylation, methylation).

In some embodiments, the RCC analysis marker is a genetic mutation, including a gene translocation, a gene inversion, a gene amplification, a gene deletion, gene aneuploidy or chromosomal aneuploidy.

In some embodiments, the RCC analysis marker is an oncogene. Oncogenes include, without limitation, PTEN, ALK, PIK3CA, MET, ROS, RET, HER2, ERG, AURKA, BRCA 1, BRCA 2, P53, RAS, RAF, EGFR, HER2, WNT, MYC, FAS, TRK, CDK, SRC, SYK, BTK and ABL.

In some embodiments, the RCC analysis marker is a positive control marker. A positive control marker can be any molecular or cellular marker expected to be present in essentially every cell in a RCC population of interest, e.g., in every RCC in a microscopic field of view. In some embodiments, the positive control marker is a chromosomal marker (e.g., a marker for human chromosomes 10, 15, 5, 3 and the like). In some embodiments, the positive control marker is a telomere marker.

In some embodiments, the determination of the presence or absence of a positive control marker is a measure for whether a cell of interest, e.g., an RCC in a microscopic field of view, is amenable to further analysis following detection of the RCC in an HD-RCC assay of this disclosure. Without wishing to be bound by theory, it is believed that RCCs that were successfully detected in (a) in a method of this disclosure, but in which a positive control maker cannot be detected in (c) in a method of this disclosure were damaged during the quenching step (b) such that these RCC are not amenable to further molecular or cellular analysis. By contrast, RCCs that were successfully identified and in which a positive control marker can be detected are amenable to further analysis.

In some embodiments, the positive control marker is determined to be present in more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, or more than 99% of the detected RCCs analyzed in (c).

The presence or absence of an RCC analysis marker in a cell can be detected using any class of marker-specific binding reagents (RCC analysis probes) known in the art, including, e.g., antibodies, aptamers, fusion proteins, such as fusion proteins including protein receptor or protein ligand components, marker-specific peptides, small molecule binders or nucleic acids (e.g., antisense oligonucleotides, hybridization probes).

The RCC analysis markers can be detected by methods such as fluorescence scanning microscopy, mass spectrometry, gene-chips, protein-chips, immunocytochemistry, whole genome sequencing and the like. In some embodiments, presence or absence of an RCC marker is detected by detecting gene copy number variants, by exome sequencing, by the mutational analysis of biomarker genes, or by polymerase chain reaction (PCR).

In some embodiments, the RCC analysis marker is a plurality of RCC analysis markers.

In some embodiments, the RCC analysis marker is a fluorescent analysis marker.

In some embodiments, the RCC analysis marker is a fluorescence in situ hybridization (FISH) marker. In some embodiments, the FISH marker is a chromosomal marker for genetic abnormalities, including, without limitation, gene fusions, aneuploidy and loss of chromosomal regions. In some embodiments, the FISH marker is a chromosomal marker for genetic mutations, including gene translocation, gene amplification and gene deletions. In some embodiments, the FISH marker is a positive control marker.

In some embodiments, the presence or absence of a FISH marker is detected using a FISH probe. In some embodiments, FISH probes comprise synthetic DNA oligonucleotides linked to a fluorescent dye. A skilled artisan will recognize that many fluorescent dyes for FISH probes are well known in the art, including, without limitation, SpectrumOrange™, SpectrumGreen™ and SpectrumAqua™. In some embodiments, the FISH-probe binds to a DNA molecule (DNA-FISH). In some embodiments, the FISH-probe binds to an RNA molecule (RNA-FISH).

FISH probes include, without limitation, locus specific probes, each of which binds to a particular region of a chromosome, alphoid or centromeric repeat probes, which are generated from repetitive sequences found on the middle of each chromosome, and whole chromosome probes, which include collections of smaller probes, each of which binds to a different sequence along the length of a given chromosome. Other FISH probes include, without limitation, whole chromosome painting probes (WPP), chromosome arm painting probes (APP), chromosome terminal band painting probes (TPP), chromosome enumeration probes (CEP), chromosome subtelomere probes (CSP) and chromosome loci specific probes (CLP), also commonly called LSI (Locus specific identifier) probes.

FISH probes can be used alone or in combination with other FISH probes or with other RCC analysis probes. Combinations of FISH probes can include more than 2 probes, more than 3 probes, more than 4 probes, more than 5 probes, more than 6 probes, more than 7 probes, more than 8 probes, more than 9 probes, more than 10 probes, more than 15 probes, more than 20 probes, more than 25 probes, more than 50 probes, more than 75 probes or more than 100 probes. In some embodiments, combinations of FISH probes include 1-color probes, 2-color probes, 3-color probes or 4-color probes.

In some embodiments, the methods further comprise contacting the RCCs with a FISH probe. In some embodiments, the RCCs are contacted with the FISH probe for more than 1 minute, more than 2 minutes, more than 3 minutes, more than 4 minutes, more than 5 minutes, more than 6 minutes, more than 7 minutes, more than 8 minutes, more than 9 minutes, more than 10 minutes, more than 15 minutes or more than 20 minutes.

In some embodiments, the RCCs are contacted with the FISH probe at a temperature of more than about 35° C., more than about 37° C., more than about 40° C., more than about 42° C., more than about 44° C. or more than about 46° C.

In some embodiments, analyzing the detected RCCs further comprises assessing the morphology of the detected RCCs. In some embodiments, the treatment of RCCs with quenching buffer does not significantly alter the morphological characteristics of the RCCs.

In some aspects, the methods of this disclosure are used to detect, quantify and characterize RCCs in non-enriched blood samples from human patients.

In some embodiments, the non-enriched blood sample is a plurality of non-enriched blood samples. In some embodiments, the RCC analysis markers are present in more than 25%, 30%, 35%, 40%, 45%, 50%, 55%, 60%, 65%, 70%, 80%, 85%, 90%, 95% or 99% of analyzed RCCs in more than 80%, 85%, 90%, 95% or 99% of blood samples in the plurality of blood samples. In some embodiments, the plurality of non-enriched blood samples was obtained from a plurality of patients.

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1: Identification, Quantification and Characterization of CTCs in Non-Enriched Blood Samples from Human Cancer Patients First, blood samples were obtained from three confirmed non-small cell lung cancer (NSCLC) patients. CTC candidates were identified in each sample as described, e.g., by Marrinucci et al. (2012) Phys Biol 9(1) 016003 or Nieva et al. (2012) Phys Biol 9(1) 016004.

Briefly, blood samples underwent red blood cell lysis followed by monolayer preparation of all nucleated cells on custom glass substrates. After paraformaldehyde (PFA) fixation and methanol permeabilization, cells were incubated with pan anti-cytokeratin antibodies recognizing cytokeratins 1, 4, 5, 6, 7, 8, 10, 13, 18 and 19 and a preconjugated anti-CD45 antibody followed by incubation with an Alexa™ 555-conjugated secondary antibody and DAPI as a nuclear stain. All nucleated cells in the specimen were imaged in multiple fluorescent channels to produce high-quality and high-resolution digital images that retain fine cytologic detail of nuclear contour and cytoplasmic distribution. Cells that were both cytokeratin positive ($CK^+$) and CD45 negative ($CD45^-$) were identified using custom computer algorithms and then subjected to morphological analysis (e.g., analysis of their nuclear-to-cytoplasmic ratio). Cells were evaluated by direct review of captured microscopic images and classified as a CTC candidate based on cell morphology (e.g., their low nuclear-to-cytoplasmic ratios) and immunophenotype (e.g., $CK^+/CD45^-$).

Example 2: FISH-Analysis of CTCs in Non-Enriched Blood Samples from Human Cancer Patients This example demonstrates that CTCs can be further analyzed with respect to their molecular or cell biology after they were identified in an HD-CTC assay. This example further demonstrates that an effective quenching buffer was identified that effectively quenched the immunofluorescent staining (e.g., the staining of immunofluorescent CTC detection markers) while maintaining the identified CTCs in a condition allowing their subsequent analysis in an fluorescent in situ hybridization (FISH) assay.

FISH Protocol Following CTC Identification by HD-CTC Assay

Following the HD-CTC assay protocol described above, the non-enriched blood samples were further processed as follows.

Cover slips were removed from the microscope slides and the slides were placed into a quenching buffer. Quenching buffers, incubation times and incubation temperatures were as further described below. The slides were then incubated for another 5 min in 5% formaldehyde in PBS. Next, the slides were transferred to 70% ethanol in water, incubated for 2 min, transferred into 85% ethanol in water, incubated for another 2 min, transferred into 100% ethanol and incubated for another 2 min. The backside and sides of the slides were wiped with a delicate task wipe and the slides were allowed to air dry. Then, 20 µl of FISH probe solution (containing, e.g., a target-gene probe, including PTEN or ERG probes, or a control probe, including centromere probes) in hybridization buffer was applied in an even line across a coverslip, the coverslip was placed probe side down onto the slide. The probe solution was allowed to spread to the borders of the cover slip and the coverslips were gently pushed to eliminate air bubbles. The borders were then sealed with rubber cement. A 10 min incubation at 83° C. (allowing for DNA denaturation) was followed by a 1-24 hour incubation at 37° C. (allowing for DNA-FISH probe hybridization). The coverslips were then removed and the slides were first placed in 0.4×SSC/0.3% Igepal solution, pH 7 for 2 minutes and afterwards transferred to 2×SSC/0.1% Igepal solution, pH 7 for 1-10 minutes. The slides were removed, the DAPI counterstain was applied and the edges of the coverslip were sealed with nail polish. Finally, the slides were analyzed by fluorescence scanning microscopy.

Comparison of Quenching Buffers

Figure 1:
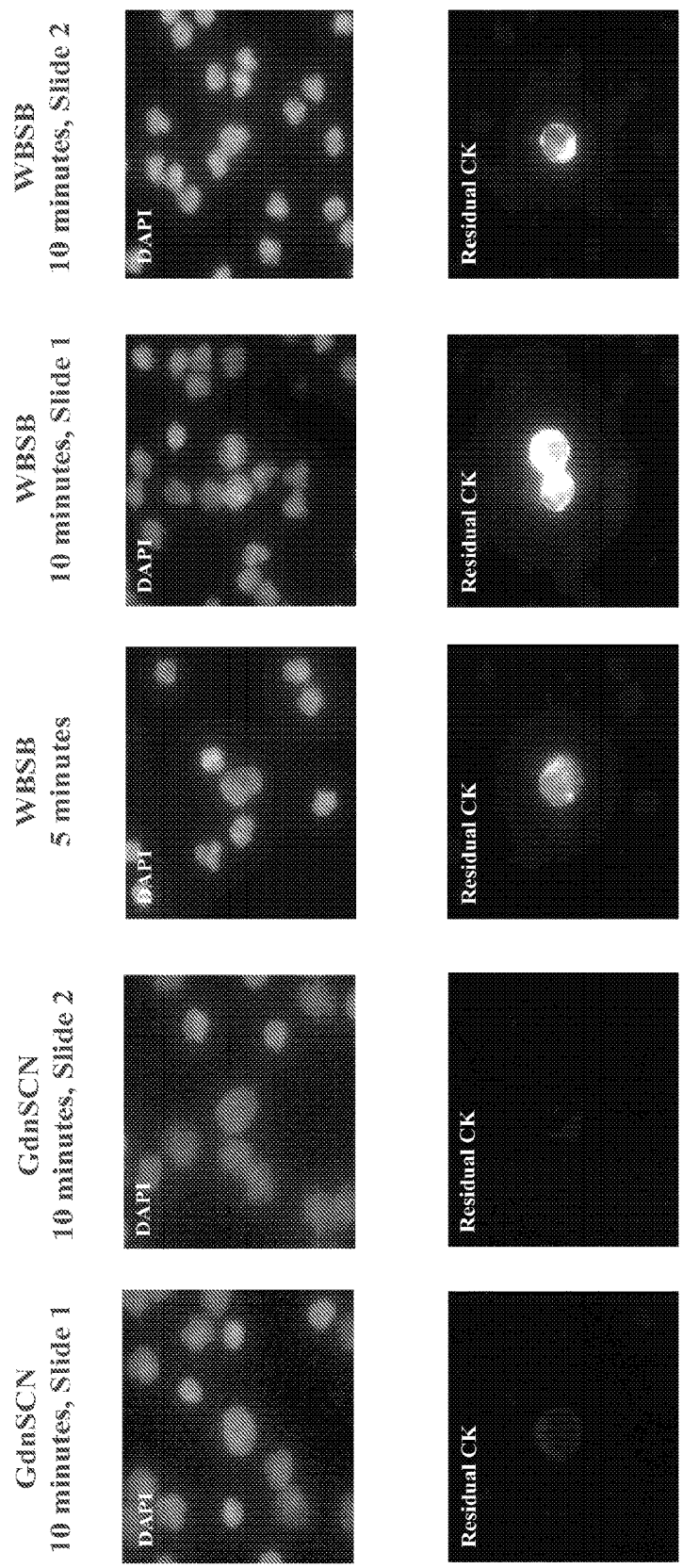
FIG. 1 shows images illustrating the relative quenching effects of Guanidinium Thiocyanate Buffer (GdnSCN) and Western Blot Stripping Buffer (WBSB) on CTC immunofluorescence staining Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (4M, 10 minutes; first and second columns) or after treatment with WBSB for 5 minutes or 10 minutes (third, fourth and fifth columns).

In exemplary experiments, the identification of CTCs in non-enriched blood samples involved the immunofluorescent detection of cytokeratin (CK). Surprisingly, incubation of CTC samples with a 4 M guanidinium thiocyanate (GdnSCN) quenching buffer resulted in an effective reduction of CK immunofluorescence while largely maintaining the CTC cell morphology (e.g., cell shapes and sizes, nuclei shapes and sizes). See, e.g., FIG. 1.

Figure 4:
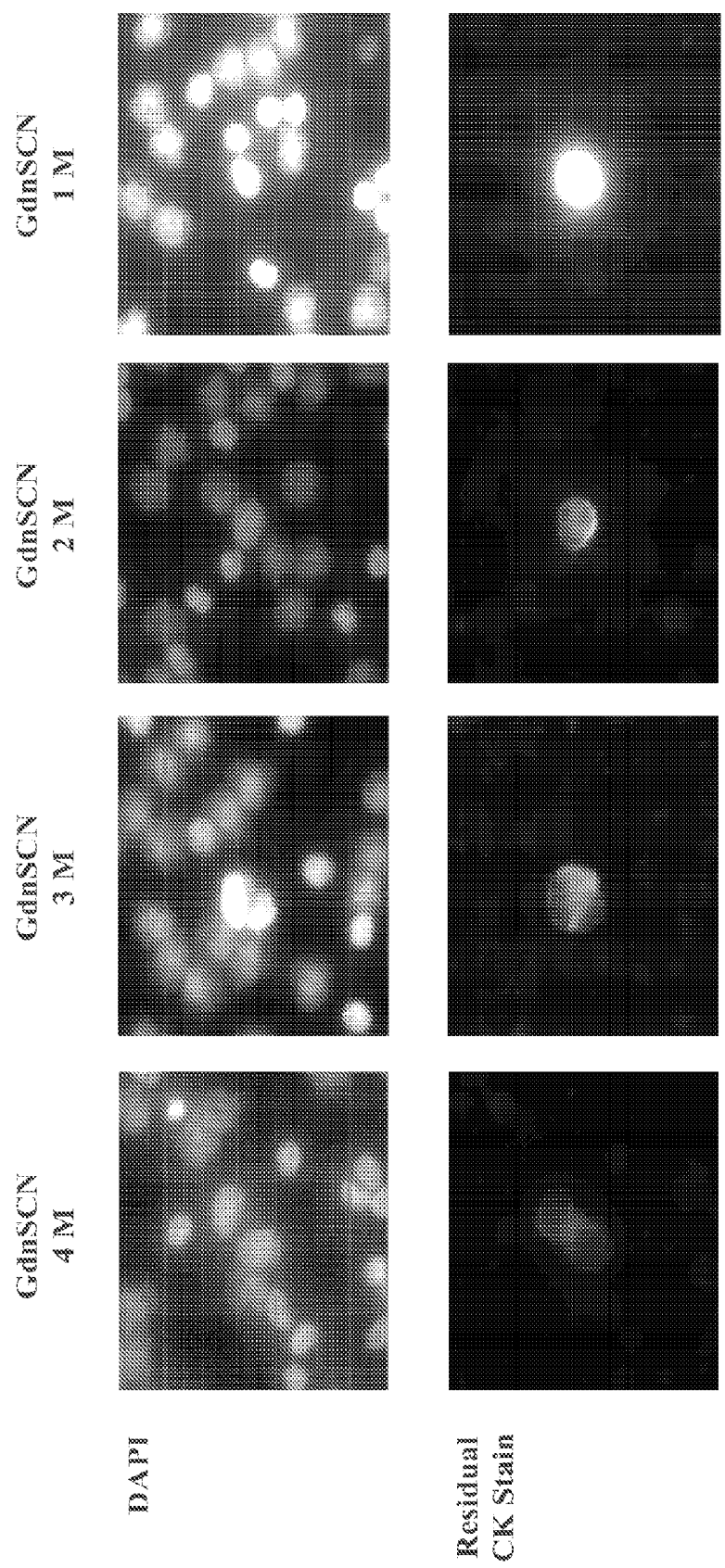
FIG. 4 shows images illustrating the concentration-dependent quenching effect of Guanidinium Thiocyanate Buffer (GdnSCN). Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN at concentrations of 4 M, 3 M, 2 M or 1M.

In typical experiments, quenching buffer incubation times around 5-10 minutes were found to be sufficient to achieve the reduction of CK immunofluorescence. Moreover, quenching buffer incubation temperatures between 4° C. and room temperature resulted in an efficient reduction of CK immunofluorescence. GdnSCN concentrations as low as 2 M were found to be sufficient to effectively reduce CK immunofluorescence. See, e.g., FIG. 4.

Quenching of CK immunofluorescence was found to be more efficient on CTCs having lower relative CK expression than in cells having higher relative CK expression. Generally, GdnSCN buffers were found to quench CK immunofluorescence by at least about 75%. In some experiments, the immunofluorescence was quenched by up to 90%, up to 99% or more.

Surprisingly, the incubation with GdnSCN buffers resulted in the retention of the majority of previously identified CTCs on the microscope slides. Generally, more than 60% of previously identified CTCs were retained. In some experiments, more than 70%, 80% and even up to 95% of previously identified CTCs were retained.

Typically, more than 85% of the retained CTCs showed signals for positive control FISH markers, such as the chromosome 10 centromere marker. In some experiments, more than 70%, 80% and even more than 95% of previously identified CTCs showed positive signals for positive control FISH markers.

Figure 3:
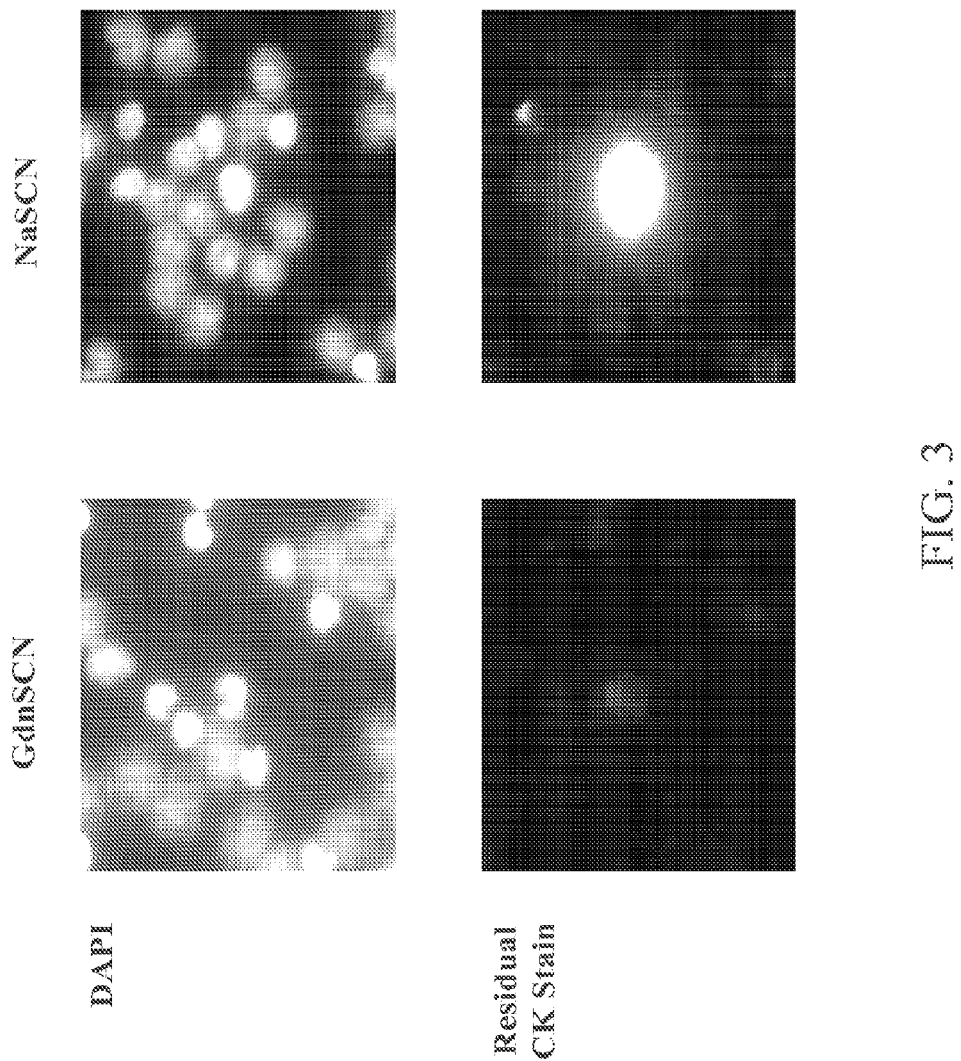
FIG. 3 shows images illustrating the relative quenching effects of Guanidinium Thiocyanate Buffer (GdnSCN, 4M) and Sodium Thiocyanate Buffer (NaSCN, 4M) on CTC immunofluorescence staining. Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (left column) or after treatment with NaSCN (right column).

The surprising activity of the GdnSCN buffer was found to depend on the presence of the chaotripic agent guanidinium. For example, sodium thiocyanate (NaSCN) buffers were found not to quench CK immunofluorescence. See, e.g., FIG. 3.

Figure 5:
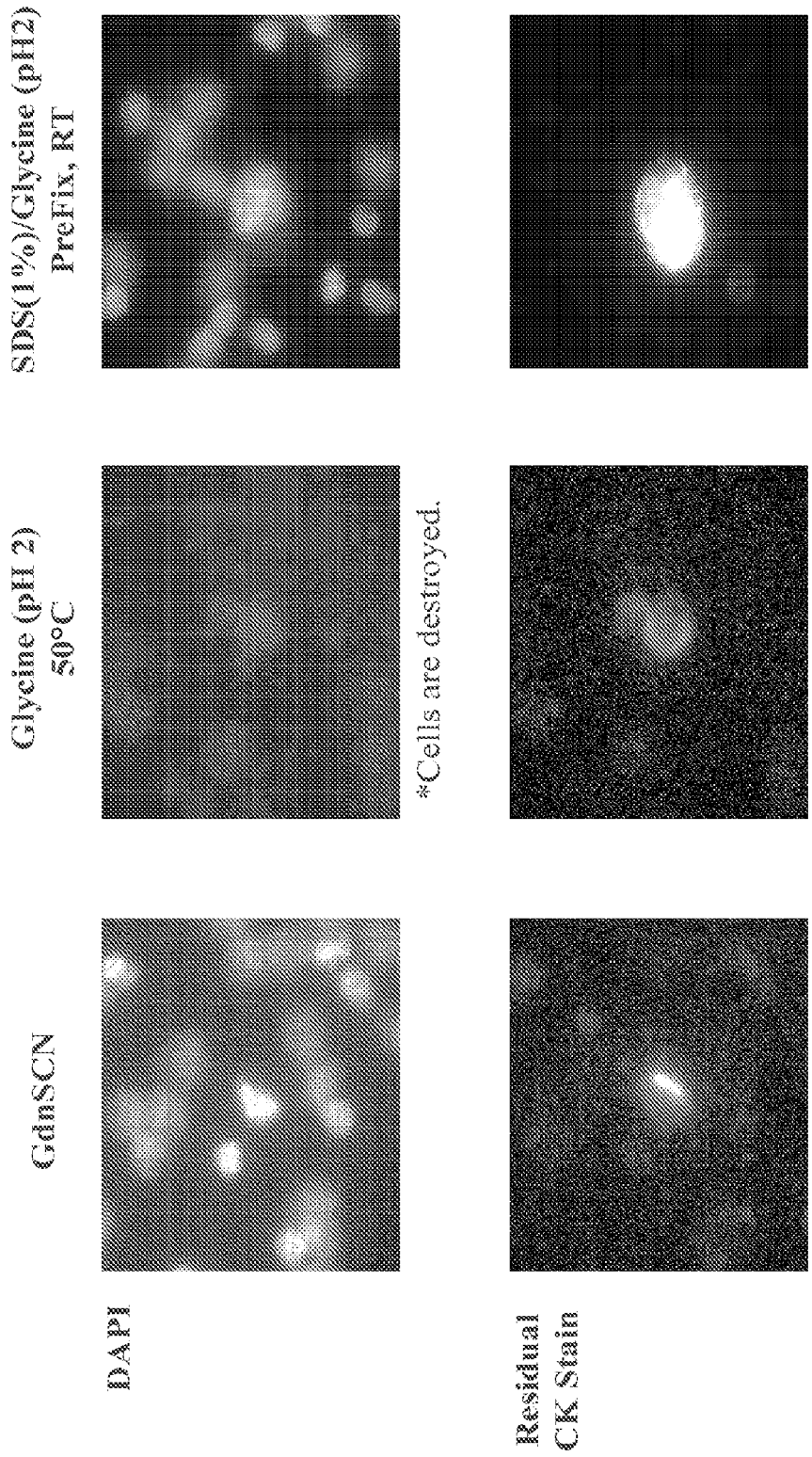
FIG. 5 shows images illustrating the relative effects of a Guanidinium Thiocyanate Buffer (GdnSCN, 4M), an acidic Glycine Buffer (pH 2) and an acidic Glycine/SDS Buffer (Pre-Fix) on CTC immunofluorescent staining and cell viability. Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (4M, left column), Glycine (pH 2, 50° C.; center column) or SDS(1%)/Glycine(pH2.2) (pre-fixed with 1% formaldehyde; right column).
Figure 6:
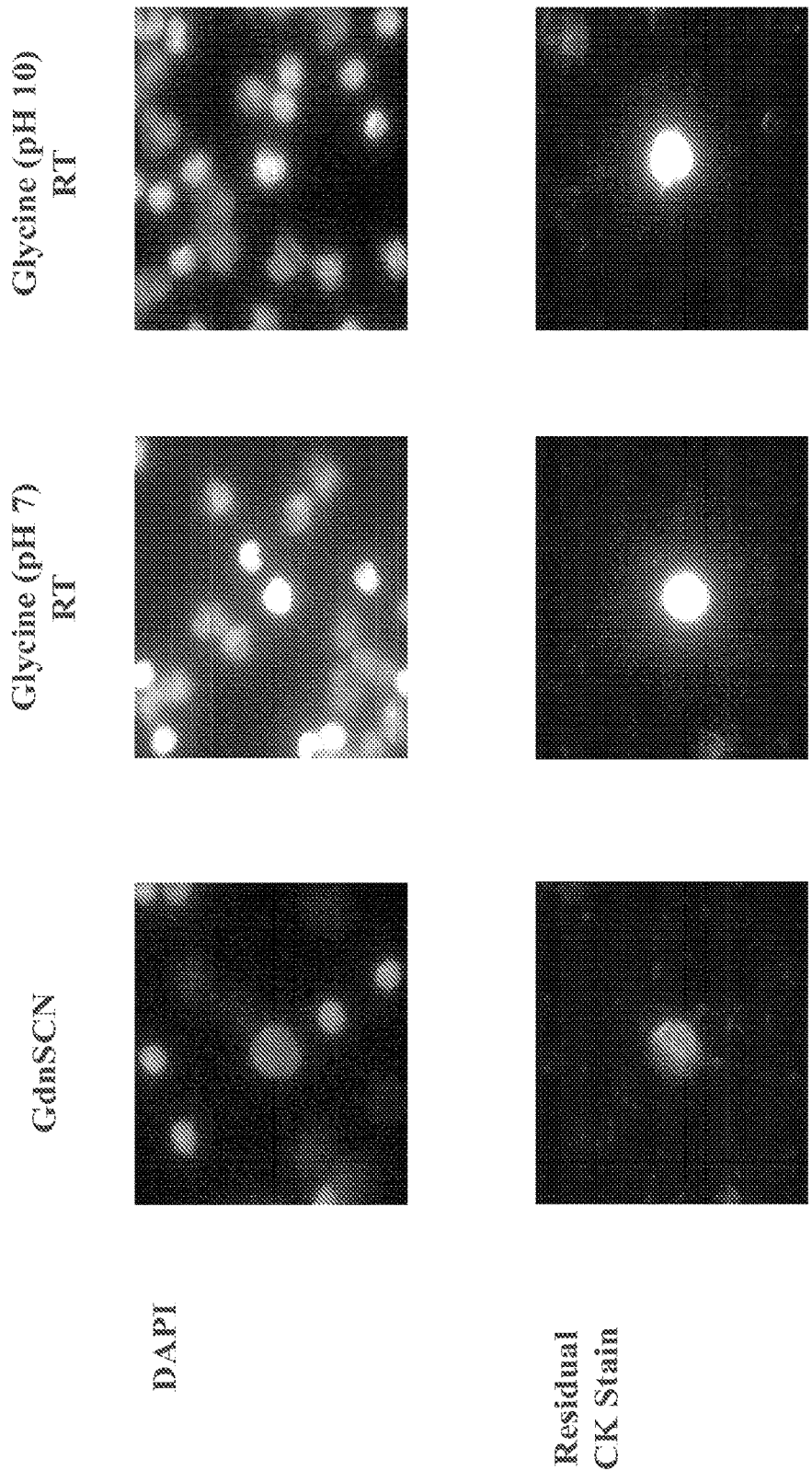
FIG. 6 shows images illustrating the relative effects of a Guanidinium Thiocyanate Buffer (GdnSCN, 4M), a neutral Glycine Buffer (pH 7) and a basic Glycine Buffer (pH 10) on CTC immunofluorescent staining and cell viability. Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (left column), Glycine (pH 2; center column) or Glycine/SDS (Pre-Fix; right column).
Figure 7:
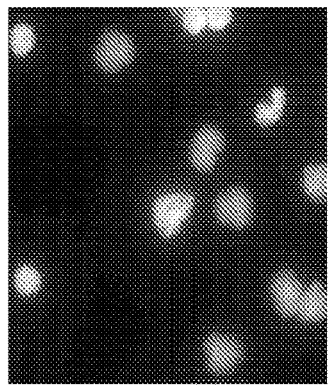
FIG. 7 shows images illustrating the relative effects of a Guanidinium Thiocyanate Buffer (GdnSCN, 4M) and an SDS(1%)/Glycine Buffer (pH 2.2) on CTC immunofluorescent staining and cell viability. Images in the top row show exemplary nuclear staining (DAPI) of WBCs and CTCs in a non-enriched blood sample. Images in the bottom row show exemplary residual cytokeratin (CK) immunofluorescence staining of CTCs after treatment with GdnSCN (left column) or SDS (1%)/Glycine (pH2.2) (room temperature; right column).
Figure 7:
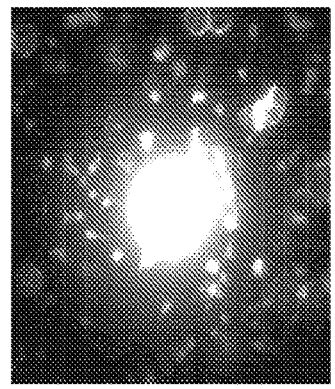
Figure 7:
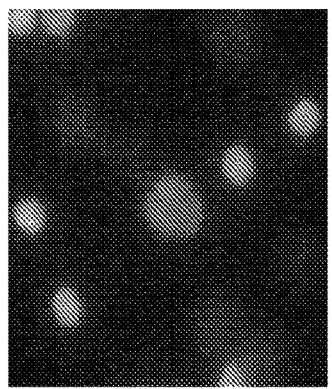
Figure 7:
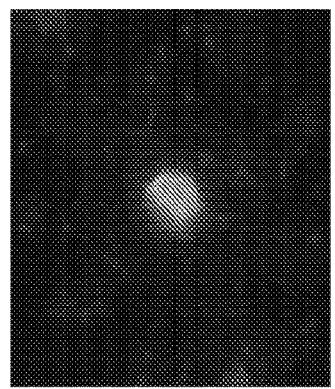

Additionally, many other buffers that are commonly used in molecular or cell biology protocols were either found to be ineffective quenchers of CK immunofluorescence (see, e.g., FIGS. 1, 2, 5, 6 and 7) or were found to destroy CTC cell morphology (see, e.g., FIG. 5, center column).

Ineffective buffers included, Sodium Thiocyanate (NaSCN), Thermo Scientific Restore™ Western Blot Stripping Buffer, Glycine/SDS at pH 2, Glycine/SDS at pH 4, Glycine/SDS at pH 7, Glycine/SDS at pH 10, and other Tris-buffers containing combinations of SDS, Tris, Betamercaptoethanol or dithiotreitol (DTT).

Figure 8:
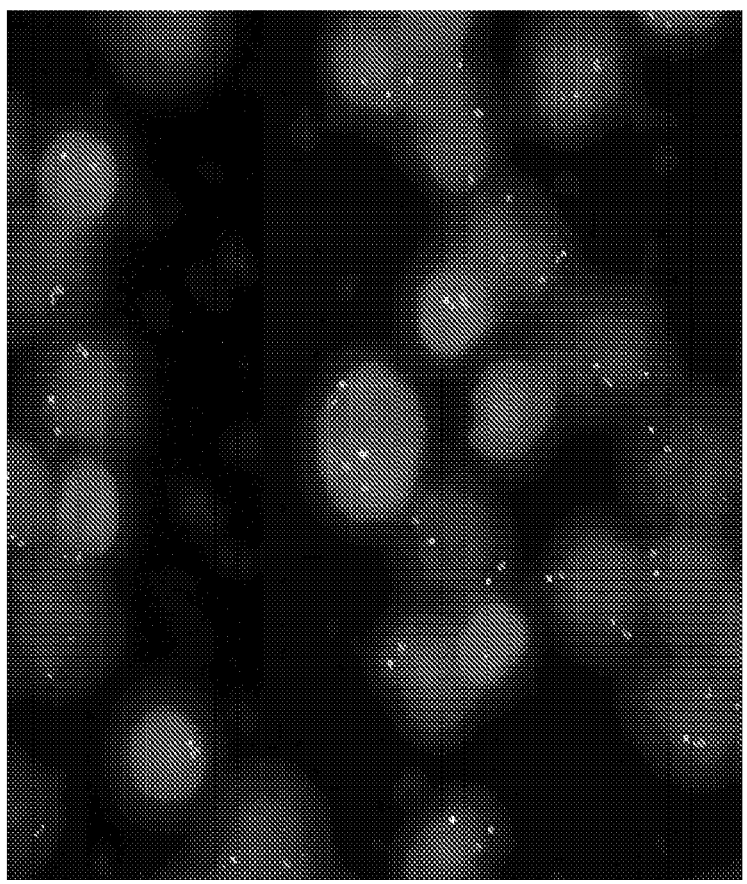
FIG. 8 shows images illustrating exemplary results of a FISH experiment conducted on a non-enriched blood sample, following the identification of CTCs in an HD-CTC assay of this disclosure and the subsequent quenching of CK-immunofluorescence with 4M GdnSCN quenching buffers. Red dots represent signals of the FISH-control probe (chromosome 10 centromere probe; Texas Red channel); green dots represent signals of FISH-probes targeting a gene of interest (PTEN; FITC channel).

Results of an exemplary FISH experiment conducted on the cells of a non-enriched blood sample following the identification of CTCs in an HD-CTC assay and the quenching of CK-immunofluorescence with 4M GdnSCN buffers are shown in FIG. 8.

In summary, guanidinium-containing buffers were found to effectively quench CTCs' immunofluorescence following their detection in HD-CTC assays while retaining the majority of identified CTCs available for further analysis and while maintaining CTC cell morphology.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claims.

What is claimed:

1. A method for analyzing rare circulating cells (RCCs) in a non-enriched blood sample, comprising: (a) detecting RCCs in the non-enriched blood sample, comprising i) determining presence or absence of one or more immunofluorescent RCC detection markers in nucleated cells in the non-enriched blood sample, and ii) assessing the morphology of the nucleated cells, wherein RCCs are detected among the nucleated cells based on a combination of distinct immunofluorescent staining and morphological characteristics; (b) quenching the immunofluorescence of the one or more immunofluorescent RCC detection markers comprising contacting the RCCs with a quenching buffer, wherein the quenching buffer comprises a chaotropic salt and wherein the immunofluorescence is quenched by more than 50%, 60%, 70%, 80%, 90%, 95%, 99%, 99.9% or 99.99%; and (c) analyzing the detected RCCs, comprising determining presence or absence of one or more fluorescent RCC analysis markers, wherein analyzing the detected RCCs comprises assessing the morphology of the detected RCCs.

2. The method of claim 1, wherein the fluorescent RCC analysis markers are fluorescence in situ hybridization (FISH) markers.

3. The method of claim 1, wherein more than 25%, 30%, 35%, 40%, 45%, 50%, 55%, 60%, 65%, 70%, 75%, 80%, 85%, 90%, 95% or 99% of RCCs detected in (a) are retained in (c).

4. The method of claim 1, wherein the fluorescent RCC analysis markers are positive control markers.

5. The method of claim 4, wherein the positive control markers are present in more than 25%, 30%, 35%, 40%, 45%, 50%, 55%, 60%, 65%, 70%, 75%, 80%, 85%, 90%, 95% or 99% of RCCs analyzed in (c).

6. The method of claim 4, wherein the positive control markers are chromosomal markers.

7. The method of claim 4, wherein the positive control markers are centromere markers or telomere markers.

8. The method of claim 1, wherein the RCC analysis markers are genetic mutations selected from the group consisting of gene translocation, gene amplification, gene deletion, gene aneuploidy and chromosomal aneuploidy.

9. The method of claim 1, wherein the RCCs are circulating tumor cells (CTCs).

10. The method of claim 1, wherein the RCCs are circulating epithelial cells (CECs).

11. The method of claim 1, wherein the RCCs are CTC mimics.

12. The method of claim 1, wherein the RCCs are CTC candidates.

13. The method of claim 1, wherein the quenching buffer comprises a chaotropic agent.

14. The method of claim 13, wherein the concentration of the chaotropic agent is at least 2M, 3M or 4M.

15. The method of claim 1, wherein the quenching buffer comprises guanidine or a guanidinium salt.

16. The method of claim 1, wherein the quenching buffer comprises guanidinium thiocyanate (guanidine thiocyanate) or guanidinium chloride (guanidine hydrochloride).

17. The method of claim 1, wherein the RCCs were contacted with the quenching buffer for a period of time of more than 1 minute, 2 minutes, 3 minutes, 4 minutes, 5 minutes, 6 minutes, 7 minutes, 8 minutes, 9 minutes, 10 minutes, 15 minutes or more than 20 minutes.

18. The method of claim 1, wherein the analyzed RCCs comprise RCC aggregates.

* * * * *